US008846850B2

(12) United States Patent
Uhrich et al.

(10) Patent No.: US 8,846,850 B2
(45) Date of Patent: Sep. 30, 2014

(54) AMPHIPHILIC MACROMOLECULES FOR NUCLEIC ACID DELIVERY

(71) Applicant: Rutgers, the State University of New Jersey, New Brunswick, NJ (US)

(72) Inventors: Kathryn E. Uhrich, New Brunswick, NJ (US); Sarah M. Sparks, New Brunswick, NJ (US); Li Gu, New Brunswick, NJ (US); Alex Harmon, New Brunswick, NJ (US); Charles M. Roth, New Brunswick, NJ (US); Carolyn Federici, New Brunswick, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/801,562

(22) Filed: Mar. 13, 2013

(65) Prior Publication Data
US 2013/0217753 A1    Aug. 22, 2013

Related U.S. Application Data

(63) Continuation-in-part of application No. 13/402,793, filed on Feb. 22, 2012, now abandoned.

(60) Provisional application No. 61/445,401, filed on Feb. 22, 2011.

(51) Int. Cl.
*C08G 73/10* (2006.01)
*A61K 48/00* (2006.01)

(52) U.S. Cl.
USPC ...................... 528/322; 514/44 R

(58) Field of Classification Search
USPC ...................... 528/322; 514/44 R
See application file for complete search history.

(56) References Cited

U.S. PATENT DOCUMENTS

| | | | |
|---|---|---|---|
| 4,065,598 A | 12/1977 | Takahashi et al. | |
| 6,328,988 B1 | 12/2001 | Uhrich | |
| 6,365,146 B1 | 4/2002 | Uhrich | |
| 6,497,895 B2 | 12/2002 | Uhrich | |
| 7,262,221 B2 | 8/2007 | Uhrich et al. | |
| 7,470,802 B2 | 12/2008 | Uhrich et al. | |
| 8,192,754 B2 | 6/2012 | Uhrich et al. | |
| 2004/0198641 A1 | 10/2004 | Uhrich et al. | |
| 2005/0089504 A1 | 4/2005 | Uhrich | |
| 2008/0057026 A1 | 3/2008 | Uhrich et al. | |
| 2011/0008396 A1 | 1/2011 | Moghe et al. | |
| 2011/0229416 A1 | 9/2011 | Uhrich et al. | |
| 2012/0022159 A1 | 1/2012 | Uhrich et al. | |
| 2012/0039983 A1 | 2/2012 | Uhrich et al. | |
| 2012/0219598 A1 | 8/2012 | Uhrich et al. | |
| 2012/0225926 A1 | 9/2012 | Uhrich et al. | |

FOREIGN PATENT DOCUMENTS

| | | |
|---|---|---|
| JP | 06145341 | 5/1994 |
| WO | WO 94/21216 | 9/1994 |
| WO | WO 00/65024 A2 | 11/2000 |
| WO | WO 01/05873 A1 | 1/2001 |
| WO | WO 03/005959 A2 | 1/2003 |
| WO | WO 03/047518 A2 | 6/2003 |
| WO | WO 03/103594 A2 | 12/2003 |

OTHER PUBLICATIONS

Sparks, Sarah M. et al., PMSE Preprints (2007), 97, 695-696.*
Aagaard et al., "RNAi therapeutics: Principoles, prospects and challenges", *Advanced Drug Delivery Reviews*, 59, 75-86 (2007).
Allen et al., "Nano-engineering block copolymer aggregates for drug delivery", *Colloids and Surfaces B: Biointerfaces* 16: 3-27 (1999).
Brannon-Peppas et al., "Nanoparticle and targeted systems for cancer therapy" *Advance Drug Delivery Reviews* 56, 1649-1659 (2004).
Burnett et al., "Current Progress of siRNA/shRNA Therapeutics in Clinical Trials", *Biotechnol. J.*, 6(9), 1130-1146 (2011).
Buyens et al., "Liposome based systems for systemic siRNA delivery: Stability in blood sets the requirements for optimal carrier design", *J. Control Release*, 158, 362-370 (2012).
Chem. Abstract of JP-6305820 (1994).
Chnari et al., "Engineered Polymeric Nanoparticles for Receptor-Targeted Blockage of Oxidized Low Density Lipoprotein Uptake and Atherogenesis in Macrophages", *Biomacromolecules*, 7, 1796-1805 (2006).
Convertine et al., "pH-Responsive Polymeric Micelle Carriers for siRNA Drugs", *Biomacromolecules* 11(11), 2904-2911 (2010).
Creusat et al., "Proton Sponge Trick for pH-Sensitive Disassembly of Polyethylenimine-Based siRNA Delivery Systems", *Bioconjug Chem.*, 21, 994-1002.
Dang et al., "Natural polymers for gene delivery and tissue engineering", *Advanced Drug Delivery Reviews*, 58, 487-499 (2006).
Davis et al., "Nanoparticle therapeutics: an emerging treatment modality for cancer", *Nature Reviews Drug Discovery*, 7, 771-782 (2008).
Djordjevic et al., "Polymeric Micelles Based on Amphiphilic Scorpion-like Macromolecules: Novel Carriers for Water-Insoluble Drugs", *Pharmaceutical Research*, 22 (1), 24-32 (2005).
Djordjevic et al., "Amphiphilic Scorpion-like Macromolecules as Micellar Nanocarriers", *Journal of Bioactive and Compatible Polymers*, 23, 532-551 (2008).
Endoh et al., "Cellular siRNA delivery using cell-penetrating peptides modified for endosomal escape", *Advanced Drug Delivery Reviews*, 61, 704-709 (2009).
Ezzat et al., "Solid formulation of cell-penetrating peptide nanocomplexes with siRNA and their stability in simulated gastric conditions", *J. Controlled Release*, 162, 1-8 (2012).
Fire et al., "Potent and specific genetic interference by double-stranded RNA in *Caenorhabditis elegans*", *Nature*, 391, 806-811 (1998).
Foged, "siRNA delivery with lipid-based systems: Promises and pitfalls", *Curr. Top. Med. Chem.*vol. 12 (2), 97-107 (2012).

(Continued)

*Primary Examiner* — Porfirio Nazario Gonzalez
*Assistant Examiner* — Kofi Adzamli
(74) *Attorney, Agent, or Firm* — Viksnins Harris & Padys PLLP

(57) ABSTRACT

The invention provides amphiphilic macromolecules that are useful for delivering nucleic acids to cells and that are useful as delivery agents for gene therapy.

24 Claims, 11 Drawing Sheets

(56) References Cited

OTHER PUBLICATIONS

Gao et al., "Research progress on siRNA delivery with nonviral carriers", *International Journal of Nanomedicine*, 6, 1017-1025 (2011).

Gu et al., "Cationic amphiphilic macromolecule-lipid complexes for in vitro siRNA delivery", 244th ACS National Meeting & Exposition, Philadelphia, PA, Abstract # 231 and corresponding Poster, 2 pages (2012).

Gu et al., "Cationic Amphiphilic Macromolecule-Lipid Complexes for in Vitro siRNA Delivery", 244th ACS National Meeting & Exposition, Philadelphia, PA, PMSE Preprint vol. 107, 365-366 (2012).

Harmon et al., "Preferential cellular uptake of amphiphilic macromolecule-lipid complexes with enhanced stability and biocompatibility", *Journal of Controlled Release*, 153(3), 233-239 (2011).

Huang et al., "Polyethylenimine grafted with diblock copolymers of polyethylene glycol and polycaprolactone as siRNA delivery vector", *J. Control Release*, 152, Suppl 1, e143-145 (2011).

Iverson, "Dual use of amphiphilic macromolecules as cholesterol efflux triggers and inhibitors of macrophage athero-inflammation", *Biomaterials*, 32, 8319-8327 (2011).

Jeong et al., "siRNA Conjugate Delivery Systems", *Bioconjugate Chemistry*, 20, 5-14 (2009).

Jung et al., "Gene silencing efficiency of siRNA-PEG conjugates: Effect of PEGylation site and PEG molecular weight", *Journal of Controlled Release*, 144, 306-313 (2010).

Kataoka et al., "Block copolymer micelles for drug delivery: design, characterization and biological significance", *Adv. Drug Deliv. Rev.* 47(1): 113-131 (2001).

Liu et al., et al., "Unimolecular micelles: Synthesis and characterization of amphiphilic polymer systems", *J. Polymer Sci: Part A: Polym. Chem.* 37(6), 703-711 (1999).

Martino et al., "Efficient siRNA Delivery by the Cationic Liposome DOTAP in Human Hematopoietic Stem Cells Differentating into Dendritic Cells", *J. Biomed. Biotechnol*, vol. 2009, 7 pages (2009).

Matsumoto et al., "Environment-Responsive Block Copolymer Micelles with a Disulfide Cross-Linked Core for Enhanced siRNA Delivery", *Biomacromolecules*, 10, 119-127 (2009).

Moore et al., "Room temperature polyesterification", *Macromolecules* 23(1): 65-70 (1990).

Nuhn et al., "Cationic Nanohydrogel Particles as Potential siRNA Carriers for Cellular Delivery", *ACS NANO*, 6(3), 2198-2214 (2012).

Otsuka et al., "Self-assembly of poly(ethylene glycol)-based block copolymers for biomedical applications", *Current Opinion in Colloid & Interface Science* 6(1): 3-10 (2001).

Sparks et al., "Efficient Intracellular siRNA Delivery by Ethyleneimine-Modified Amphiphilic Macromolecules", *Macromol. Biosci.*, 11, 1192-1200 (2011).

Sundaram et al., "Interplay of polyethyleneimine molecular weight and oligonucleotide backbone chemistry in the dynamics of antisense activity", *Nucleic Acids Res.*, 35(13), 4396-4408 (2007).

Tao et al., "Novel amphiphilic macromolecules and their in vitro characterization as stabilized micellar drug delivery systems", *Journal of Colloid and Interface Science*, 298, 102-110 (2006).

Tian et al., "Design andsynthesis of amphiphillic poly(ethylene glycol) derivatives as a micellar drug delivery system", *Polymer Preprints*, 43(2), 719-720 (2002).

Tian et al., "Design and synthesis of amphiphilic poly(ethylene glycol) derivatives as a micellar drug delivery system", *Abstracts of Papers, Part 2*, 224, (1-2), abstract 748, 224th ACS National Meeting (2002).

Tian et al., "Amphiphilic Scorpion-like Macromolecules: Design, Synthesis, and Characterization", *Macromolecules*, 37, 538-543 (2004).

Torchilin, "Structure and design of polymeric surfactant-based drug delivery systems", *J. Control Release* 73(2-3): 137-172 (2001).

Tseng et al., "Lipid-based systemic delivery of siRNA", *Adv. Drug Delivery Rev.*, 61(9), 721-731 (2009).

Uhrich et al., "Cationic Amphiphilic Macromolecules (CAMs)-Lipid Complexes for Intracellular siRNA Delivery", 2013 Controlled Release Society Annual Meeting, Emerging Technologies, Abstract# 95, 2 pages (2013).

Wang et al., "A peptide-targeted delivery system with pH-sensitive amphiphilic cell siRNA delivery", *J. Control Release*, 134, 207-213 (2009).

Whitehead et al., "Synergistric silencing combinations of lipid-like materials for efficacious siRNA delivery", *Mol. Ther.*, 19(9), 1688-1694 (2011).

Wong et al., "Polymer systems for gene delivery—Past, present, and future", *Progress in Polymer Science*, 32, 799-837 (2007).

Zhang et al., "Cationic lipids and polymers mediated vectors for delivery of siRNA", *Journal of Controlled Release*, 123 1-10 (2007).

Zhang et al., "DC-Chol/DOPE cationic liposomes: A comparative study of the delivery", *Int. J. Pharm*, 390, 198-207 (2010).

Chnari et al., "Nanoscale anionic macromolecules for selective retention of low-density lipoproteins", Biomaterials, vol. 26, pp. 3749-3758, 2005.

Chnari et al., "Nanoscale anionic macromolecules can inhibit cellular uptake of differentially oxidized LDL", Biomacromolecules, vol. 7, pp. 597-603, 2006.

Geall, et al., "Synthesis of Cholesteryl Polyamine Carbamates: $pK_a$ Studies and Condensation of Calf Thymus DNA", *Bioconjugate Chem.*, 11, 314 (2000).

Harmon et al., "In Vitro Evaluation of Amphiphilic Macromolecular Nanocarriers for Systemic Drug Delivery", Journal of Bioactive and Compatible Polymers, 24, pp. 185-197, 2009.

Iverson et al., "Controllable inhibition of cellular uptake of oxidized low-density lipoprotein: structure-function relationships for nanoscale amphiphilic polymers", Acta Biomater., 6(8), pp. 3081-3091, 2010.

Liu, et al., "New Poly(D-glucaramidoamine)s Induce DNA Nanoparticle Formation and Efficient Gene Delivery into Mammalian Cells", *Journal of the American Chemical Society*, 126, 7422-7423 (2004).

Liu, et al., "Hydroxyl Stereochemistry and Amine Number within Poly(glycoamidoamine)s Affect Intracellular DNA Delivery", *Journal of the American Chemical Society*, 127, 3004-3015 (2005).

Liu, et al., "Poly(glycoamidoamine)s for Gene Delivery. Structural Effects on Cellular Internalization, Buffering Capacity, and Gene Expression", *Bioconjugate Chem.*, 18, 19-30 (2007).

Plourde et al., "Structure—Activity Relations of Nanolipoblockers with the Atherogenic Domain of Human Macrophage Scavenger Receptor A" *Biomacromolecules*, 10, 13 81-1391, 2009.

Reineke, "Poly(glycoamidoamine)s: Cationic glycopolymers for DNA delivery", *Journal of Polymer Science: Part A: Polymer Chemistry*, 44, 6895-6908 (2006).

Sparks, SM "Design, Synthesis, and Utility of Functionalized Nanoscale Amphiphilic Macromolecules for Biomedical Applications", PhD Dissertation, Rutgers, The State University of New Jersey, 198 pages (2011).

Sparks, SM "Design, Synthesis, and Utility of Functionalized Nanoscale Amphiphilic Macromolecules for Biomedical Applications", Thesis Defense Presentation, Rutgers, The State University of New Jersey, 51 pages (2010).

Sparks, et al., "Amphiphilic Scorpion-Like Macromolecules: Novel Vectors for Gene Delivery", poster presented at Union College, 5 pages (2007).

Sparks et al., "Synthesis of functionalized amphiphilic scorpion-like macromolecules for biomedical applications", The 234th ACS National Meeting, Boston, MA, poster and corresponding abstract, PMSE 391, 6 pages, (2007).

(56) References Cited

OTHER PUBLICATIONS

Sparks, et al., "Synthesis of functionalized amphiphilic scorpion-like macromolecules for biomedical applications", *Polymeric Materials: Science & Engineering*, 97, 695-696 (2007).

Sparks, et al., "Life after Union: Polymers-R-Us", Presentation at Union College, 40 pages (2007).

Srinivasachari, et al., "Trehalose Click Polymers Inhibit Nanoparticle Aggregation and Promote pDNA Delivery in Serum", *Journal of the American Chemical Society*, 128, 8176-8174 (2006).

Steege, et al., "Local Polarity and Microviscosity in the Hydrophobic Cores of Amphiphilic Star-like and Scorpion-like Macromolecules", Macromolecules, 40, 3739-3748 (2007).

Wang et al., "Nanoscale amphiphilic macromolecules as lipoprotein inhibitors: the role of charge and architecture", Int. J. Nanomedicine, 2(4), pp. 697-705, 2007.

Wang et al., "Comparison of PEG chain length and density on amphiphilic macromolecular nanocarriers: Self-assembled and unimolecular micelles", Acta Biomaterialia, 5, pp. 883-892, 2009.

\* cited by examiner

US 8,846,850 B2

AMPHIPHILIC MACROMOLECULES FOR NUCLEIC ACID DELIVERY

CROSS-REFERENCE TO RELATED APPLICATION(S)

This application is a continuation-in-part of U.S. patent application Ser. No. 13/402,793, filed Feb. 22, 2012, and this application claims the benefit of priority of U.S. Provisional Application No. 61/445,401, filed Feb. 22, 2011; these applications are incorporated by reference herein in their entirety.

GOVERNMENT FUNDING

The invention described herein was made with government support under Grant Number NIH R01 HL107913 awarded by the National Institutes of Health. The United States Government has certain rights in the invention.

BACKGROUND OF THE INVENTION

The use of novel amphiphilic macromolecules (AMs) for drug delivery has been an area of recent interest. Nanoscale amphiphilic macromolecules (AMs) are biocompatible amphiphilic polymers composed of an alkylated sugar backbone covalently linked to poly(ethylene glycol) (PEG). In aqueous solution, AMs self-assemble to form 10-20 nm micelles with critical micelle concentrations as low as 100 nM, making them more stable than other common micelles. In addition, the basic structure of AMs has multiple points of modification such that the polymer can be modified and evaluated for virtually any application.

These polymers were first designed and synthesized by L. Tian, L. Yam, N. Zhou, H. Tat, and K. Uhrich, *Macromolecules* 2004, 37, 538. Since their initial synthesis, AMs have been evaluated for the delivery of cancer therapeutics and for the inhibition of highly oxidized low-density lipoprotein in macrophage cells.

Currently, the most efficacious systems to deliver nucleic acids are viruses. However, as they are viruses, they may be unsafe for use as they will provoke an immune response. Thus, novel, versatile, and effective synthetic systems to deliver nucleic acids are needed. Currently, there is a lack of effective systems that are biocompatible and versatile.

SUMMARY OF THE INVENTION

Applicant has now functionalized AMs for nucleic acid delivery. The AMs of the invention are biocompatible and are useful for delivering a variety of nucleic acids efficiently.

In one embodiment the invention provides a compound of formula I:

wherein:

B is absent or the group —NH(-A-NH—)$_n$—(CH$_2$)$_2$—NH—C(=O)-D-;

each A is independently an ethylene group that is optionally substituted with one or more (C$_1$-C$_3$)alkyl groups;

D is (C$_1$-C$_6$)alkyl m is an integer from 0 to 500;

n is an integer from 0 to 500;

p is an integer from 1 to 500; and each r is independently an integer from 0 to 20;

or a salt thereof.

In another embodiment the invention provides a composition comprising a compound of formula I or a salt thereof and a nucleic acid (e.g. DNA, RNA or siRNA).

In another embodiment, the invention provides a pharmaceutical composition comprising a compound of formula I or a pharmaceutically acceptable salt thereof and a nucleic acid (e.g. DNA, RNA or siRNA) and a pharmaceutically acceptable carrier.

In another embodiment, the invention provides a composition comprising a compound of formula I or a salt thereof and a lipid and a nucleic acid (e.g. DNA, RNA or siRNA).

In another embodiment, the invention provides a pharmaceutical composition comprising a compound of formula I or a pharmaceutically acceptable salt thereof and a lipid and a nucleic acid (e.g. DNA, RNA or siRNA) and a pharmaceutically acceptable carrier.

In another embodiment, the invention provides a method for delivering a nucleic acid (e.g. DNA, RNA or siRNA) into a cell comprising contacting the cell with a composition comprising a compound of formula I or a salt thereof and the nucleic acid under conditions such that the nucleic acid is delivered into the cell.

In another embodiment, the invention provides a method for delivering a nucleic acid (e.g. DNA, RNA or siRNA) into a cell comprising contacting the cell with a composition comprising a compound of formula I or a salt thereof and a lipid and the nucleic acid under conditions such that the nucleic acid is delivered into the cell.

The invention also provides processes and intermediates disclosed herein that are useful for preparing compounds of formula (I) or salts thereof.

DETAILED DESCRIPTION

Figure 1:
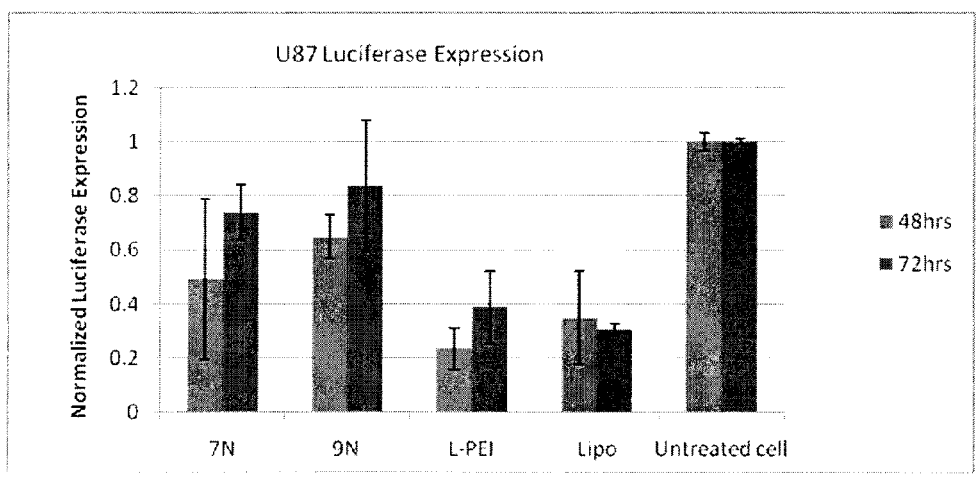
FIG. 1 shows the U87 luciferase transfection assay at time points of 48 and 72 hrs for compound 7N (i.e. compound 7 nM), compound 9N, linear-polyethylenimine (L-PEI) and lipofectamine (Lipo). For each compound, the 48 h timepoint is on the left and the 72 h timepoint is on the right.

Specific values listed below for radicals, substituents, and ranges, are for illustration only; they do not exclude other defined values or other values within defined ranges for the radicals and substituents. The term "alkyl" includes both straight and branched alkyls.

In one embodiment, the compound of formula I is a compound of formula I':

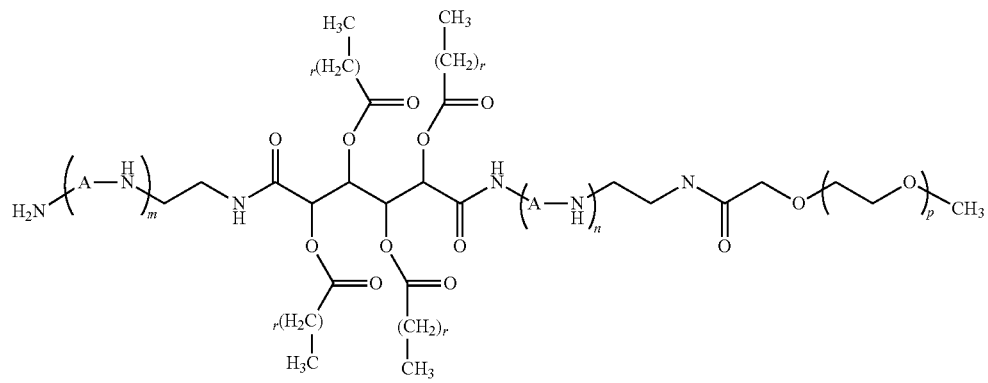

wherein:
each A is independently an ethylene group that is optionally substituted with one or more $(C_1-C_3)$alkyl groups;
m is an integer from 0 to 500;
n is an integer from 0 to 500;
p is an integer from 1 to 500; and
each r is independently an integer from 0 to 20;
or a salt thereof.

In one embodiment the compound of formula I is not a compound of the following formula:

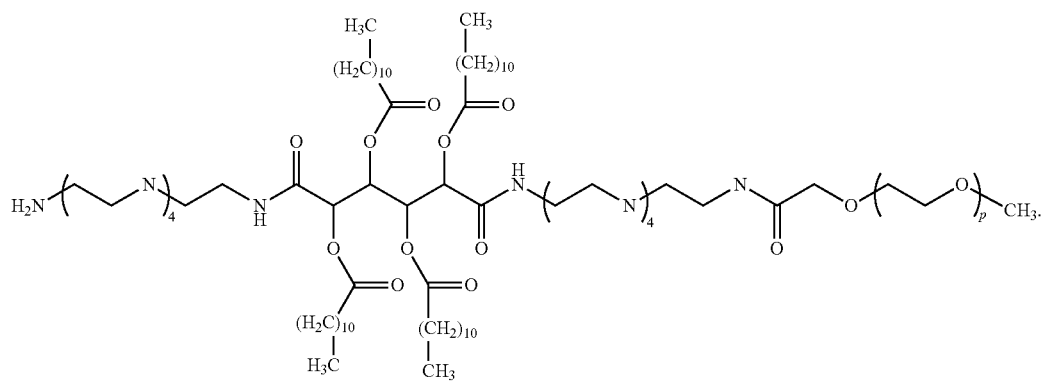

In one embodiment the compound of formula (I) is a compound of formula (Ia):

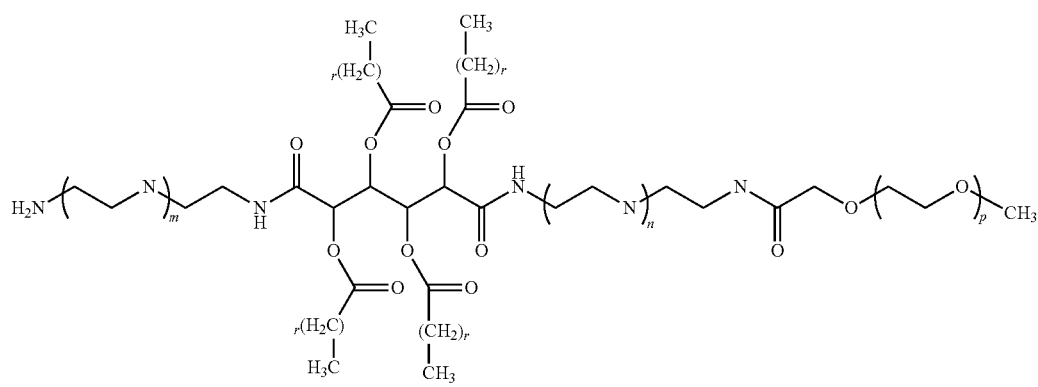

wherein:
m is an integer from 0 to 500;
n is an integer from 0 to 500;
p is an integer from 1 to 500; and
each r is independently an integer from 0 to 20; or a salt thereof.

In one embodiment, the compound of formula I is a compound of formula

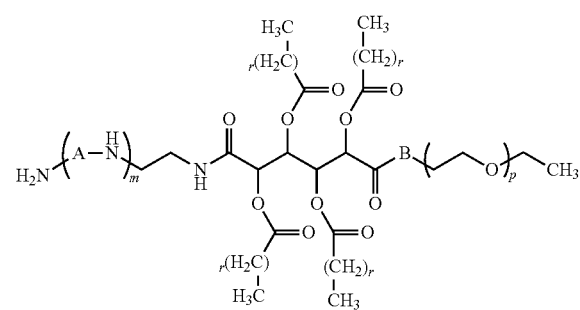

wherein:
B is absent or the group —NH(-A-NH—)$_n$—(CH$_2$)$_2$—NH—C(=O)—CH$_2$—;
each A is independently an ethylene group that is optionally substituted with one or more (C$_1$-C$_3$)alkyl groups;
m is an integer from 0 to 500;
n is an integer from 0 to 500;
p is an integer from 1 to 500; and
each r is independently an integer from 0 to 20; or a salt thereof.

In one embodiment m is an integer from 1 to 200.
In one embodiment m is an integer from 1 to 100.
In one embodiment m is an integer from 1 to 20.
In one embodiment m is 1, 2, 3, or 4.
In one embodiment m is 3.
In one embodiment n is an integer from 1 to 200.
In one embodiment n is an integer from 1 to 100.
In one embodiment n is an integer from 1 to 20.
In one embodiment n is 1, 2, 3, or 4.
In one embodiment n is 3.
In one embodiment p is an integer from 20 to 200.
In one embodiment p is an integer from 20 to 100.
In one embodiment p is an integer from 40 to 80.
In one embodiment p is about 109.
In one embodiment each r is independently an integer from 0 to 20.
In one embodiment each r is independently an integer from 1 to 20.
In one embodiment each r is independently 6, 7, 8, 9, 10, 11, 12, 13, 14, or 15.
In one embodiment each r is 8, 9, 10, 11, or 12.
In one embodiment each r is 10.
In one embodiment m is 2, 3, 4, or 5; n is 2, 3, 4, or 5; p is an integer from about 95 to about 125; and each r is independently 6, 7, 8, 9, 10, 11, 12, 13, 14, or 15.

In one embodiment the compound of formula (I) is a compound of the following formula (Ib):

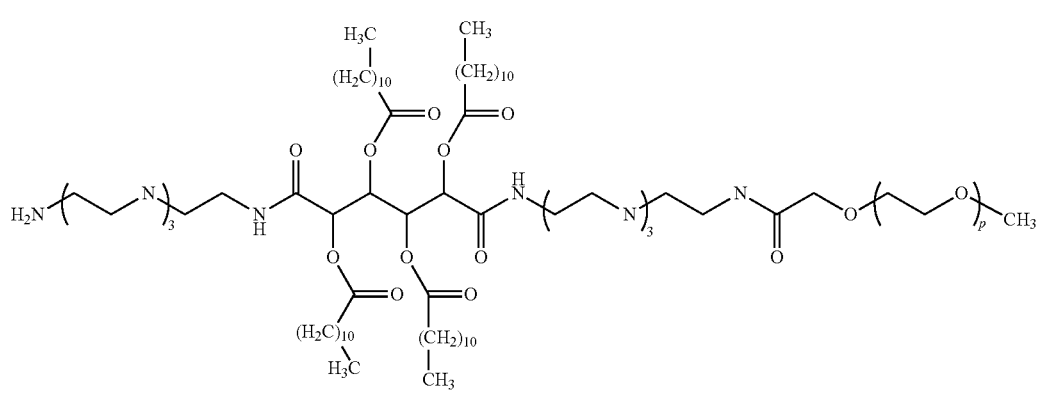

or a salt thereof.

In one embodiment for a compound of formula (Ib), p is an integer from about 20 to about 200.
In one embodiment one embodiment for a compound of formula (Ib), p is about 109.
In one embodiment the compound of the invention is a compound of the following formula:
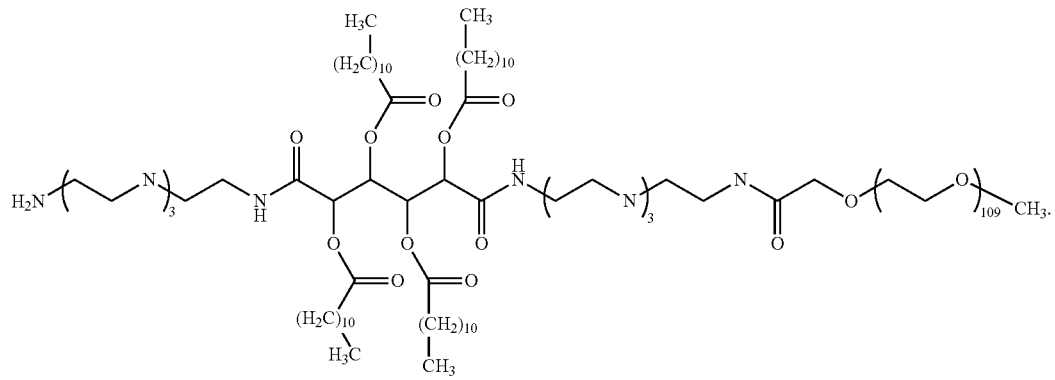
or a salt thereof.
In one embodiment the compound of the invention is a compound selected from:
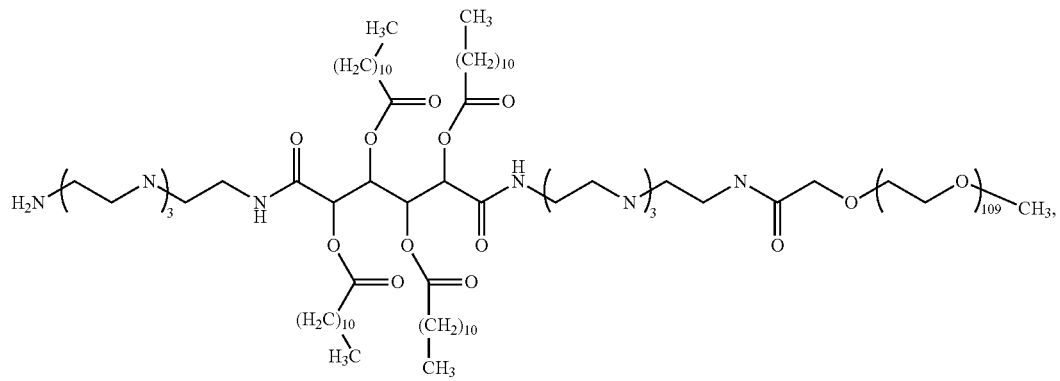
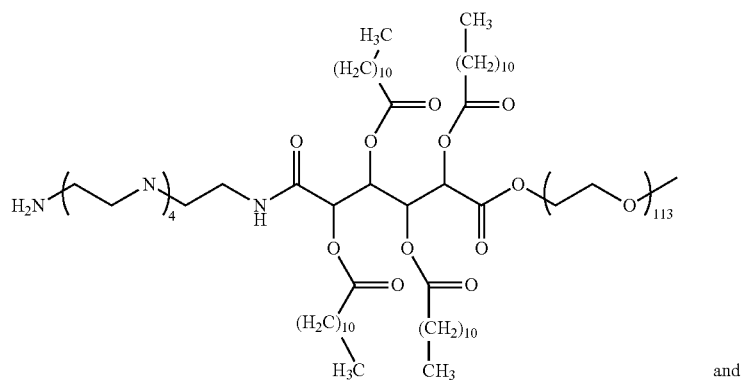
and

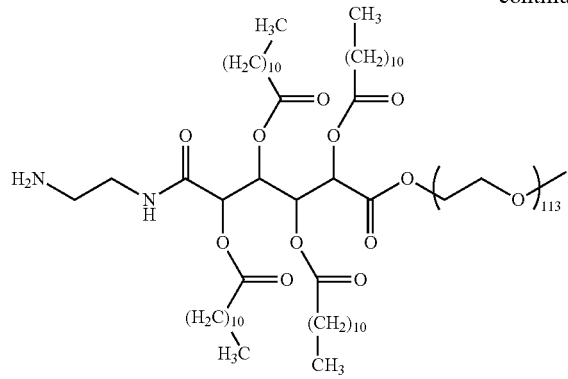
or a salt thereof.
In one embodiment the compound of formula I is not a compound of formula:
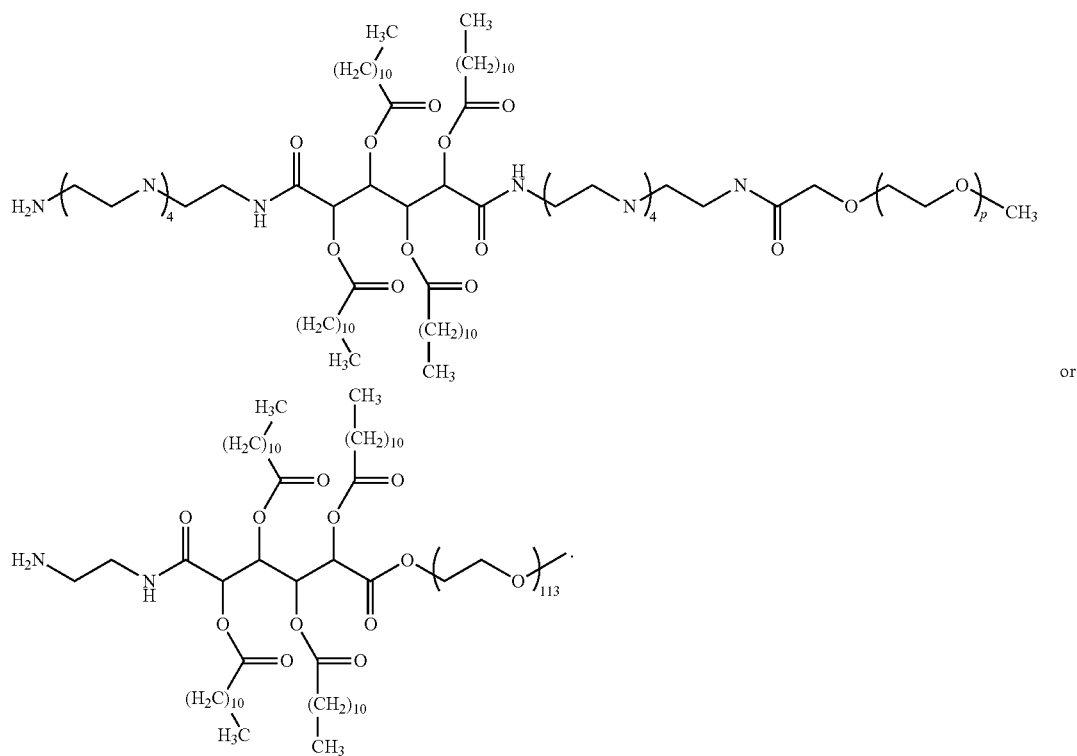
In one embodiment the compound of formula I is not a compound of formula:
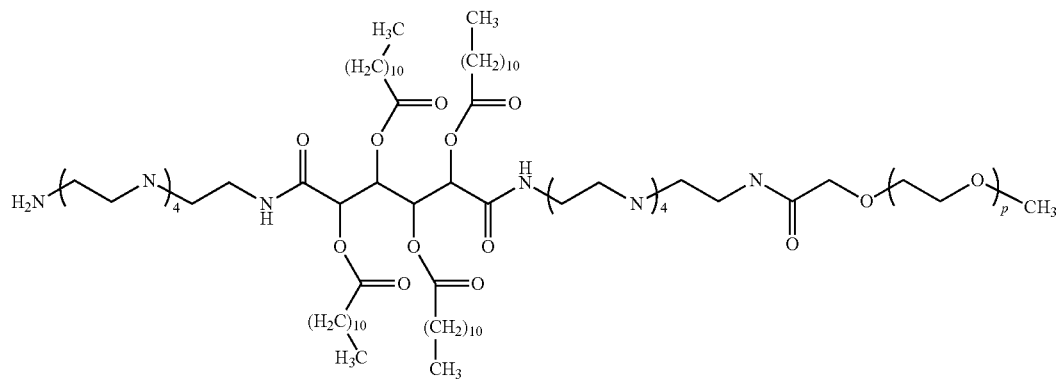

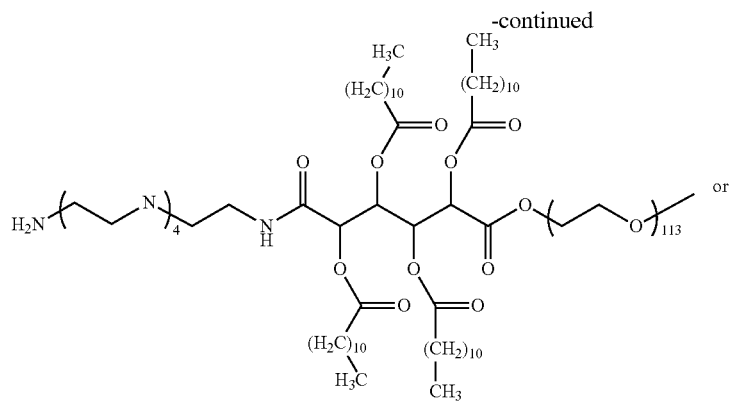
or
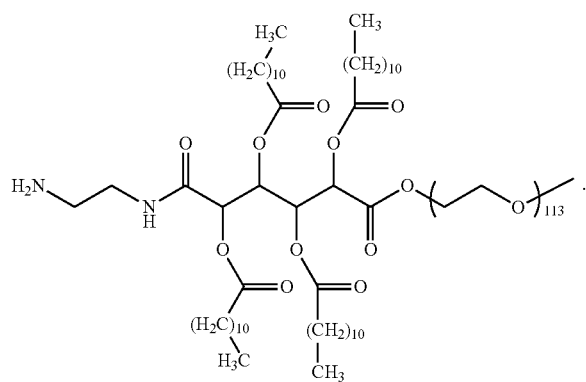
In one embodiment the compound of formula I is not a compound of formula:
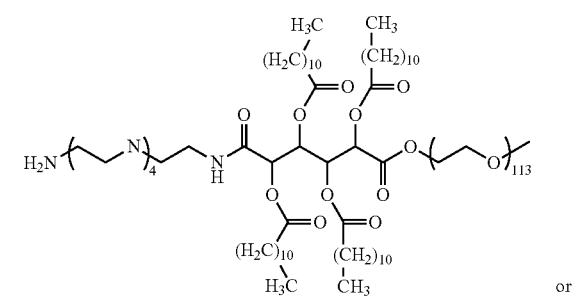
or
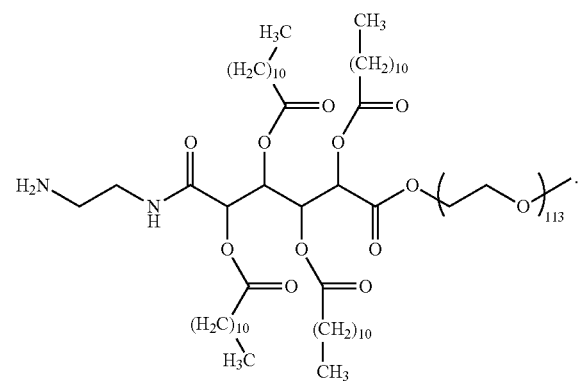
In one embodiment the compound of formula I is not a compound of formula:
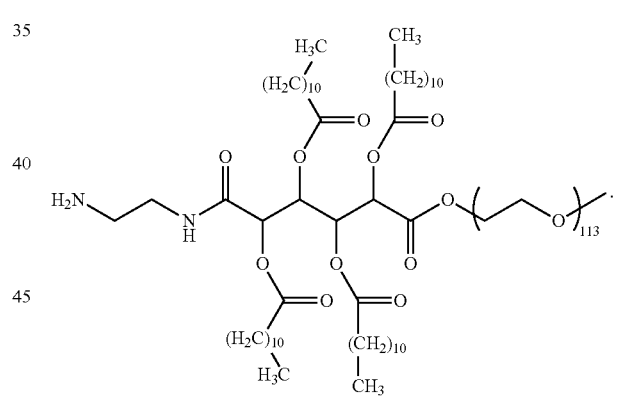
In one embodiment the compound of formula I is not a compound of formula:
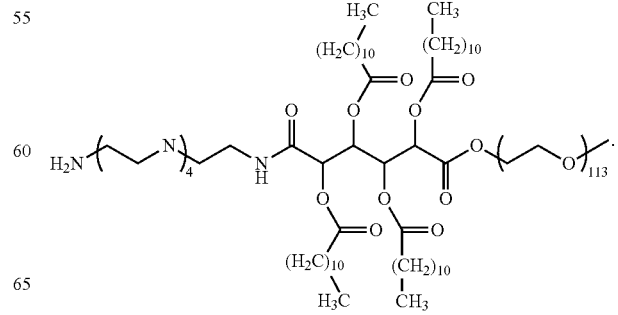

In one embodiment the compound of formula I is not a compound of formula:
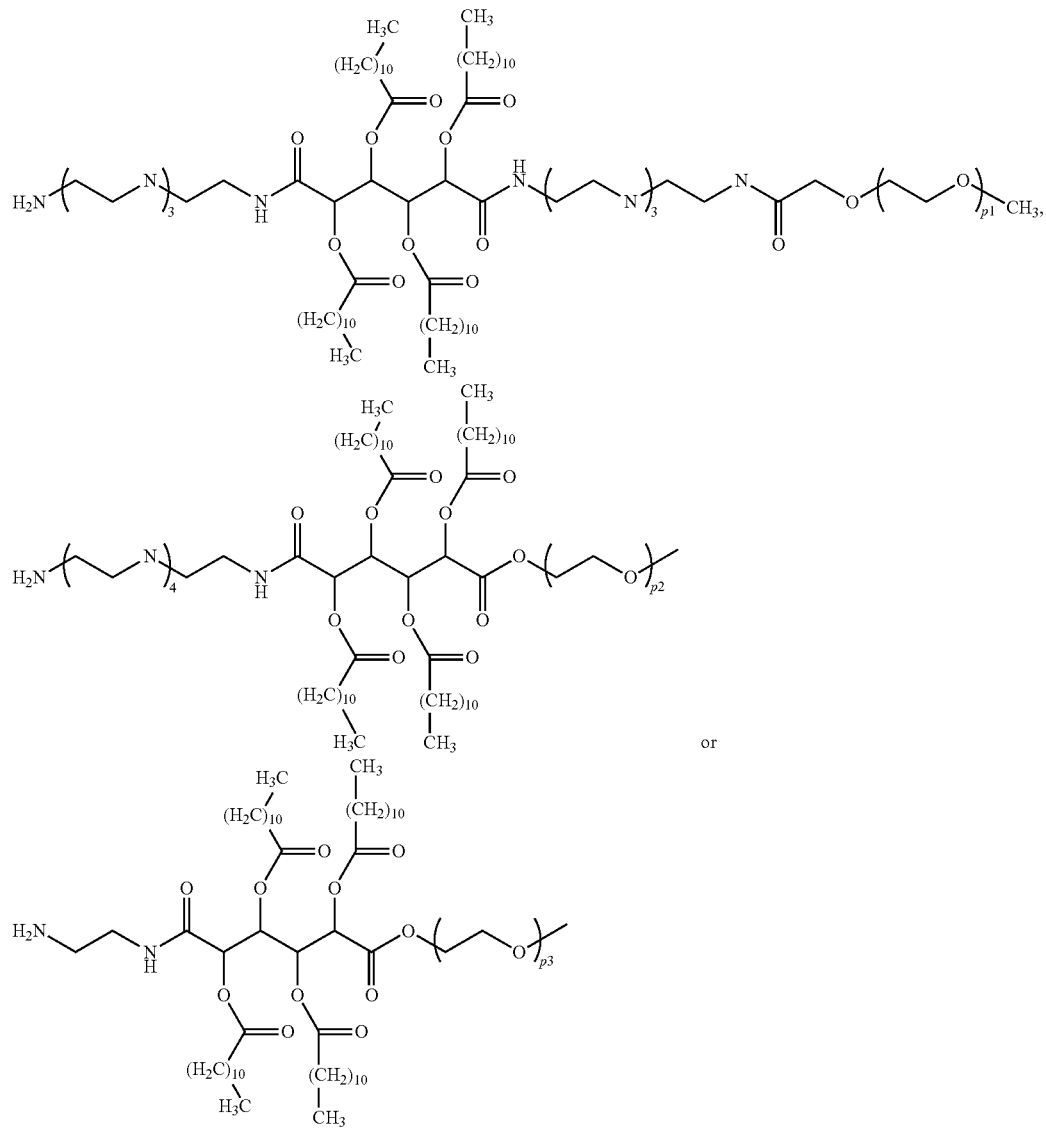
wherein p1 is about 109; p2 is about 113; and p3 is about 113; or a salt thereof.
In one embodiment the compound of formula I is not a compound of formula:
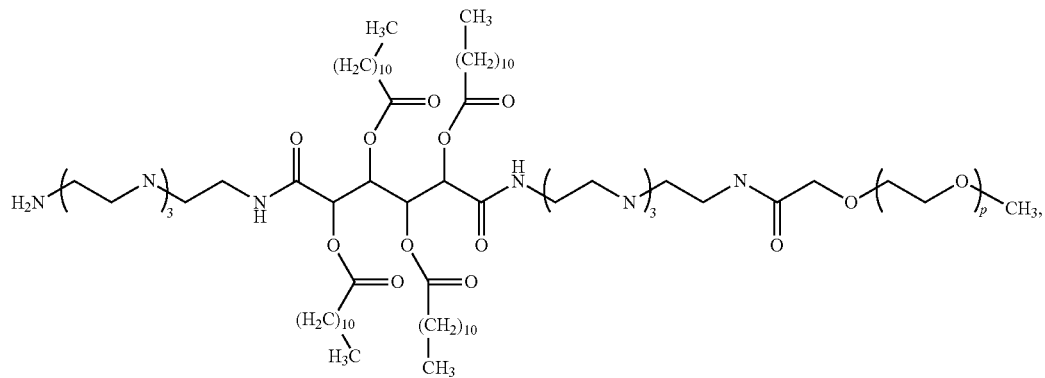

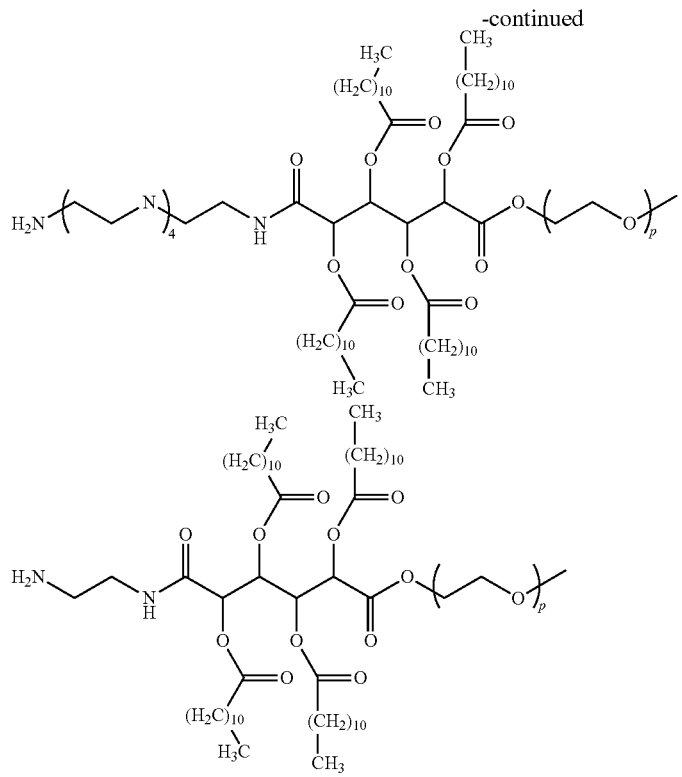

or

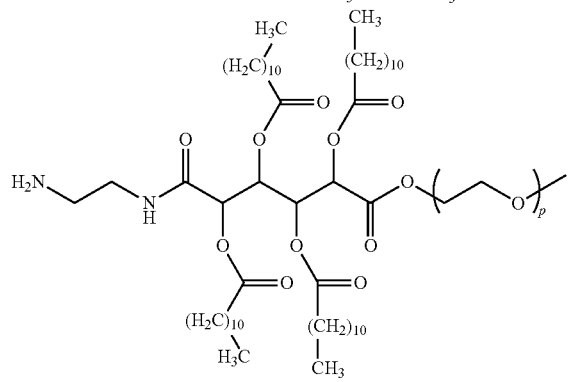

wherein each p is independently an integer from 1 to 500; or a salt thereof.

In one embodiment the value for B is absent (i.e. the carbonyl adjacent to B and the oxygen adjacent to B are connected (for the compound of formula I)).

In one embodiment the value for B is the group —NH(-A-NH—)$_n$—(CH$_2$)$_2$—NH—C(=O)—CH$_2$—.

It is to be understood that the group —NH(-A-NH—)$_n$—(CH$_2$)$_2$—NH—C(=O)—CH$_2$— is the structure:

wherein the wavy lines represent points of attachment to the compound of formula I.

It also to be understood that when the group —NH(-A-NH—)$_n$—(CH$_2$)$_2$—NH—C(O)—CH$_2$— for B is included in the compound of formula I the group is incorporated into the compound of formula I as drawn (e.g. the —NH part of the B group is on the left hand side and bonded to the carbonyl of the compound of formula I and the CH$_2$— part of the B group is on the right and side and bonded to the oxygen atom of the PEG group of the compound of formula I).

In one embodiment B is absent or the group —NH(-A-NH—)$_n$—(CH$_2$)$_2$—NH—C(=O)—CH$_2$—.

In one embodiment D is —CH$_2$—.
In one embodiment D is —CH$_2$CH$_2$—.
In one embodiment D is —CH$_2$CH$_2$CH$_2$—.
In one embodiment D is —CH$_2$CH(CH$_3$)CH$_2$—.
In one embodiment D is —CH$_2$CH$_2$CH$_2$CH$_2$—.
In one embodiment D is —CH$_2$CH$_2$CH$_2$CH$_2$CH$_2$—.
In one embodiment D is —CH$_2$CH$_2$CH$_2$CH$_2$CH$_2$CH$_2$—.

In one embodiment the nucleic acid is DNA, RNA or a siRNA molecule.

In one embodiment the nucleic acid is DNA.
In one embodiment the nucleic acid is RNA.
In one embodiment the nucleic acid is a siRNA molecule.

A compound of formula I can be prepared using procedures similar to those described in L. Tian, L. Yam, N. Zhou, H. Tat, and K. Uhrich, *Macromolecules* 2004, 37, 538, or using the procedures described herein.

The term "alkyl" includes both straight and branched hydrocarbon groups.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The following terms are used to describe the sequence relationships between two or more nucleotide sequences: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, JMB, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, certain embodiments of the invention provide nucleic acid molecules that are substantially identical to the nucleic acid molecules described herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In addition to the chemical optimization of stringency conditions, analytical models and algorithms can be applied to hybridization data-sets (e.g. microarray data) to improve stringency.

The present invention further provides a method of substantially silencing a target gene of interest or targeted allele for the gene of interest in order to provide a biological or therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect. As used herein, the term "biological effect" refers to a change in the behavior of a cell, tissue or organism. Biological effects encompass a wide range of behaviors that include but are not limited to changes in gene expression, metabolism, growth, motility, or response to environmental perturbations. Biological effects can be measured by a qualified scientist or technician using assays specific to the biological effect under study.

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest, for example, huntingtin. As used herein, the term "siRNA" is a generic term that encompasses the subset of shRNAs and miRNAs. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding ataxin-1 or huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase. In one embodiment, the compound may be at least 51% a single isomer (enantiomer or diastereomer). In another embodiment, the compound may be at least 60% a single isomer (enantiomer or diastereomer). In another embodiment, the compound may be at least 80% a single isomer (enantiomer or diastereomer). In another embodiment, the compound may be at least 90% a single isomer (enantiomer or diastereomer). In another embodiment, the compound may be at least 95% a single isomer (enantiomer or diastereomer). In another embodiment, the compound may be at least 99% a single isomer (enantiomer or diastereomer).

The compositions of the invention (e.g. compounds of formula I and a nucleic acid) can be formulated as pharmaceutical compositions and administered to a mammalian host, such as a human patient in a variety of forms adapted to the chosen route of administration, i.e. orally, parenterally, by intravenous, intramuscular, topical or subcutaneous routes. Thus, the compositions of the invention may be systemically administered, in combination with a pharmaceutically acceptable vehicle such as an inert diluent.

The compositions of the invention may be administered intravenously or intraperitoneally by infusion or injection. Solutions of the compositions can be prepared, for example, in water. Under ordinary conditions of storage and use, these preparations may contain a preservative to prevent the growth of microorganisms.

The pharmaceutical dosage forms suitable for injection or infusion should be sterile, fluid and stable under the conditions of manufacture and storage. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the encapsulates of the invention in the required amount in the appropriate solvent with various of the other ingredients enumerated above, as required, followed by sterilization.

The dose and method of administration will vary from animal to animal and be dependent upon such factors as the type of animal being treated, its sex, weight, diet, concurrent medication, overall clinical condition, the particular therapeutic agent employed, the specific use for which the agent is employed, and other factors which those skilled in the relevant field will recognize.

Therapeutically effective dosages may be determined by either in vitro or in vivo methods. For each particular dosage form of the present invention, individual determinations may be made to determine the optimal dosage required. The range of therapeutically effective dosages will naturally be influenced by the route of administration, the therapeutic objectives, and the condition of the patient. The determination of effective dosage levels, that is, the dosage levels necessary to achieve the desired result, will be within the ambit of one skilled in the art. Typically, applications of agent are commenced at lower dosage levels, with dosage levels being increased until the desired effect is achieved.

The invention also includes complexes (e.g. liposomes) comprising a compound of formula I or a salt thereof and one or more lipids. Such AM/lipid complexes and compositions thereof are useful for the delivery of nucleic acids (e.g. DNA, RNA or siRNA).

Useful lipids include 1,2-dioleoyl-sn-glycero-3-phosphoethanolamine (DOPE) and 1,2-dioleoyl-3-trimethylammonium-propane (DOTAP). Other lipids include, but at not limited to, N-[1-(2,3-dioleyloxy)propyl]-N,N,N-trimethylammoniumchloride (DOTMA), dioleoyl phosphatidyl choline (DOPC), dioctadecylamidoglicylspermin (DOGS), 2,3-dioleoyloxy-N-[2-(spermine-carboxamido)ethyl]-N,N-dimethyl-1-propanaminum (DOSPA), 1,2-distearoyl-3-dimethylammonium-propane (DODAP), 1,2-Bis(diphenylphosphino)ethane (dppe), Dimethyldioctadecylammonium-Bromide Salt (DDAB). Theses lipids can be used alone, or as a mixture with one or more lipids. The mass ratio of the mixture can be equal or unequal.

The AM/lipid complexes can be formed from a compound of formula I and one or more lipids. The complexes can include different ratios of lipids. For example, when two lipids are present the weight ratios of the two lipids to one another can be 9:1, 4:1, 7:3, 3:2 or 1:1 or any useful ratio to obtain the desired properties. The ratio of the cationic AMs (i.e. compounds of formula I) to the lipids can also be varied. For example, the weight ratios of the AMs to lipids can be 0:1, 1:10, 1:5, 1:2, 1:1, 2:1, 5:1, 10:1 and 1:0.

The invention will now be illustrated by the following non-limiting Examples.

EXAMPLES

Example 1

A Cationic Polymer for Nucleic Acid Delivery

A representative compound (polymer) of the invention was prepared and evaluated as a nucleic acid delivery vehicle by measuring its hydrodynamic diameter and its zeta potential.

The compound 7 nM was synthesized as shown in Scheme A3.1. In this synthetic method, the formation of oligomers is controlled by stoichiometry and the slow addition of the starting materials via the syringe pump.

Scheme A3.1. Synthesis of 7nM.

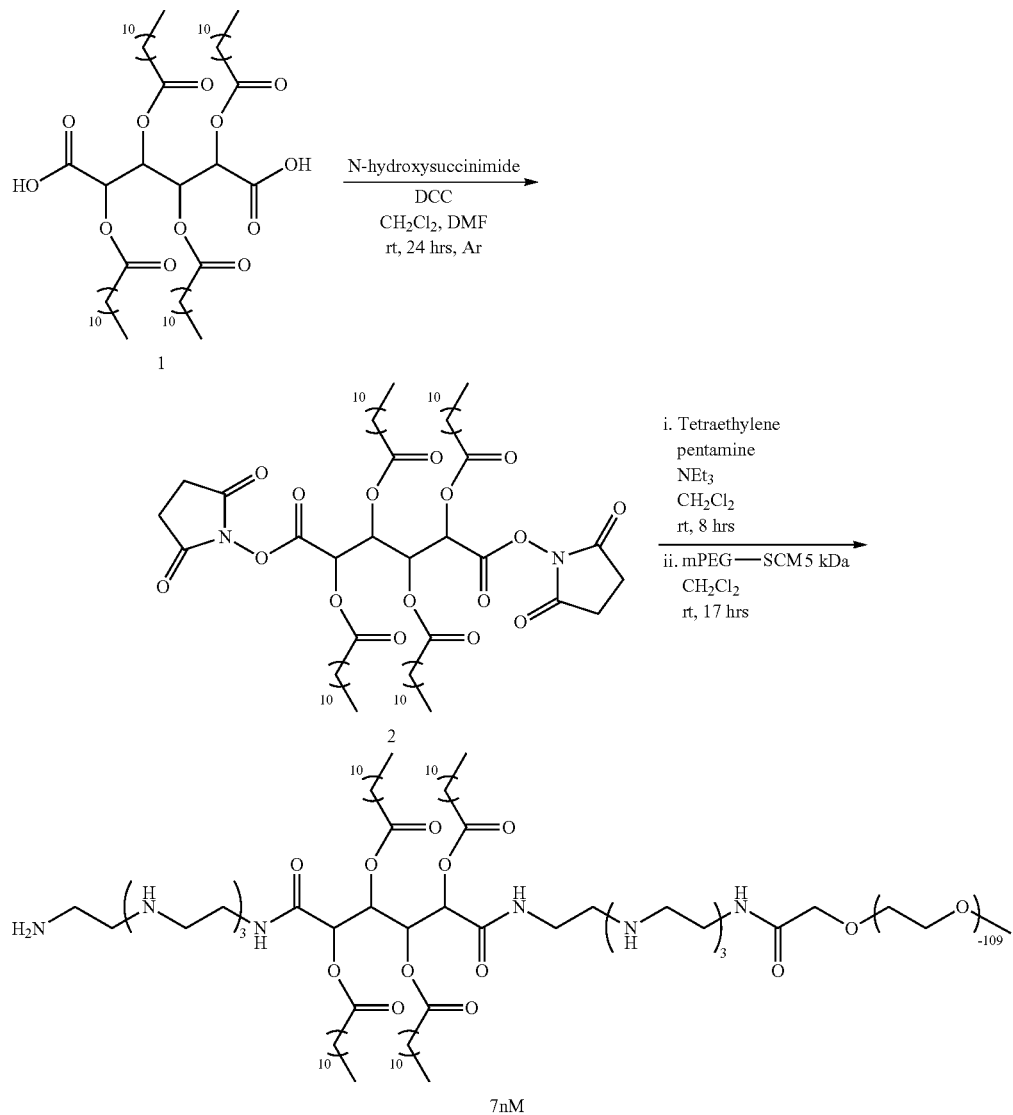

7nM

Successful synthesis of the polymer was verified by proton nuclear magnetic resonance ($^1$H NMR) spectroscopy and the molecular weight was determined by gel permeation chromatography (GPC) relative to PEG standards. Due to the abundance of PEG in the polymer (~83% of protons), the presence of new protons in the $^1$H NMR spectra were difficult to detect, particularly from 0.8 to 2.4 ppm where the methylene protons of the hydrophobic chains comprise the majority of that region. Thus, the spectra were monitored for the disappearance of the protons of the activating group (N-hydroxysuccinimide) on 2, which resonate at 2.8 ppm. In addition, a new, broad peak resonating at ~2.30 ppm for the ethylene spacer indicated successful conjugation of the tetraethylene pentamine to the polymer. However, integrations indicated that there was a mixture of di-PEGylated polymer and mono-PEGylated polymer (i.e. 2 PEGs to 4 alkylated arms).

The polymer was further characterized by dynamic light scattering for its ability to form micelles and by zeta potential to confirm a cationic polymer was indeed obtained. The hydrodynamic diameter was determined to be 92.2±39.4 nm while the zeta potential was 30.7±2.9 mV. The large positive magnitude of the zeta potential suggests that this polymer is a good candidate for delivering nucleic acids (e.g. siRNA).

Example 2

Alternative Route to Compound 7 nM

In Example 1, the only control over the formation of oligomers is the stoichiometry and the slow addition of the starting materials using the syringe pump. To better control the synthesis of these polymers and isolate a more pure product, two protection schemes were designed and evaluated.

To control the final structure of 7 nM, a protection step was added to the synthetic procedure. As a model synthesis, only 7 nM was evaluated. The protection step, the addition of benzyl chloroformate (CBZ-Cl) was added following the addition of tetraethylene pentamine to 2, as shown in Scheme A3.2. It should be noted that an effort was made to isolate and purify 3, but once it was isolated as a white solid, it was insoluble in further solvents for chemical characterization. Thus, in the final synthesis, it was not isolated. The CBZ protecting group was removed by hydrogenation in the final step of the synthesis.

In comparison to the 7 nM synthesized in Example 1, the ¹H NMR of 7 nM_2 from Example 2 had several differences. Specifically, in the spectra for 7 nM, the broad peak at 2.30 ppm was assigned to the ethylenes of the tetraethylene pentamine groups. However, in the spectra for 7 nM_2 from Example 2, two new, distinct peaks were observed and assigned to the ethylenes of the tetraethylene pentamine groups and the hydrogens of the alkylated arms on the mucic acid derivative, which are shifted downfield due to the amino groups. The first was a quartet at 3.12 ppm integrating for ~22 protons and the second a quartet at ~1.42 ppm integrating for ~32 protons. The number of protons is due to overlap of the ethylenes of the tetraethylene pentamine groups with some methylenes of the alkylated arms, which shift downfield due to interactions with the electronegative amino groups (the peak that normally exists at ~2.4 ppm integrating for 8 protons is no longer there). In addition, a broad peak at 12.2 ppm integrating for 7 protons was assigned the amino hydrogens.

The polymer was further characterized by dynamic light scattering for its ability to form micelles and by zeta potential to confirm a cationic polymer was indeed obtained. The hydrodynamic diameter was determined to be 174.4±42.5 nm while the zeta potential was 24.9±3.1 mV. Thus, this synthetic procedure appears to be a viable method for preparing compound 7 nM.

Scheme A3.2. Synthesis of 7nM_2 utilizing one CBZ—Cl protection step.

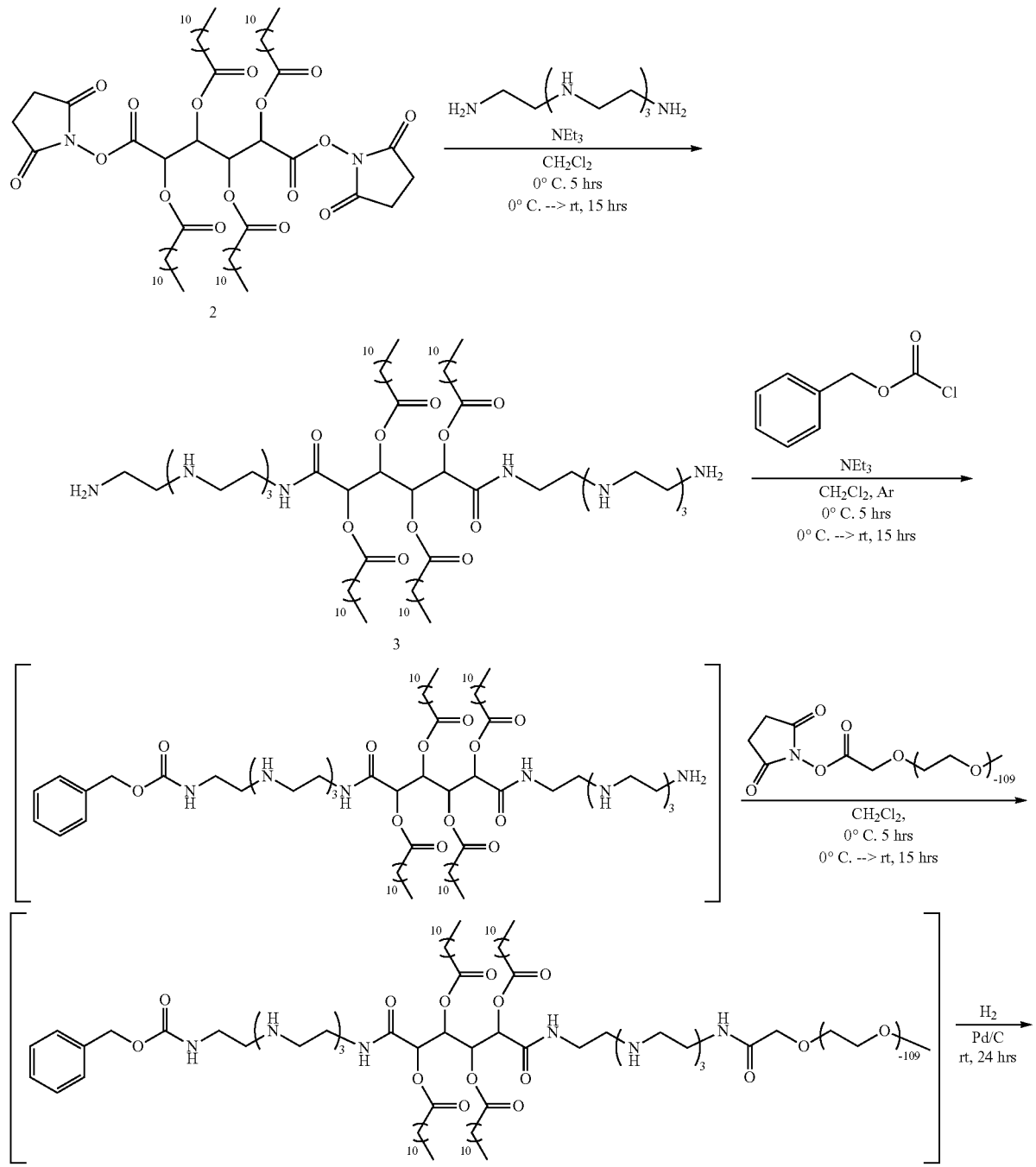

-continued

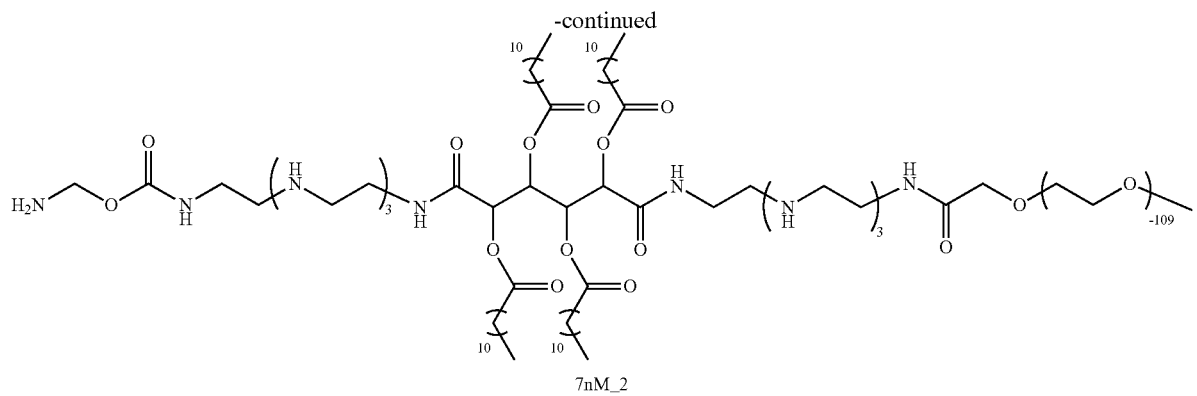

7nM_2

Example 3

Evaluation of the siRNA Delivery Efficacy of Compound 7N (Compound 7N is the Same Compound as Compound 7 nM) and 9N (Compound 9N is Described in Example 5)

The siRNA delivery efficacy of the cationic AM complexes was tested using a human primary glioblastoma cell line (U87 MG). By loading the cationoic AMs complexes with anti-luciferase siRNA at N/P ratio of 50, knockdown of luciferase expression was achieved and quantified at 48 hrs and 72 hrs. FIG. 1 shows the knockdown efficacy of compounds 7N and 9N compared to linear-polyethylenimine (L-PEI) and lipofectamine (Lipo). It has been demonstrated that cationic AMs have lower cytotoxicity than the L-PEI and lipofectramine

Example 4

Preparation and Evaluation of AM-Lipid Complexes

Figure 2:
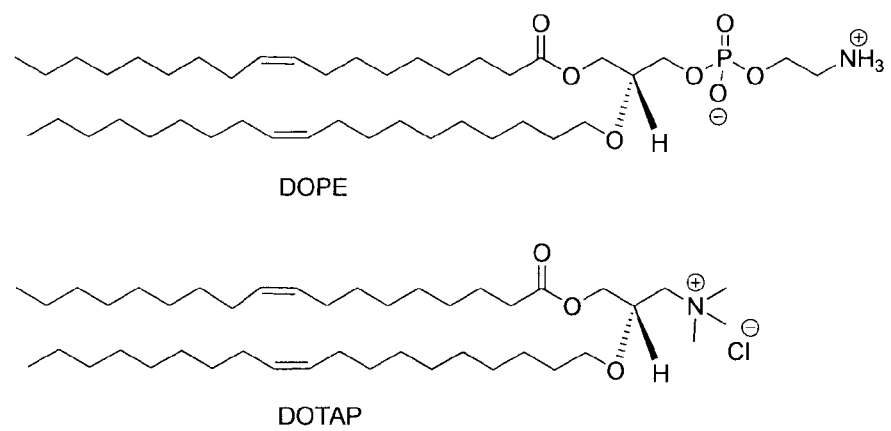
FIG. 2 depicts the structures of DOPE and DOTAP.

AM-lipid complexes were prepared by incorporating cationic AMs compound 7N (i.e. compound 7 nM) or compound 9N into liposomes composed of 1,2-dioleoyl-sn-glycero-3-phosphoethanolamine (DOPE) and 1,2-dioleoyl-3-trimethy-lammonium-propane (DOTAP) at a 1:1 weight ratio of DOPE:DOTAP (FIG. 2). The cationic AMs were incorporated into the DOPE:DOTAP liposomes at various AM:lipid ratios using well-established methods (Harmon, A. M., et al., Preferential cellular uptake of amphiphilic macromolecule-lipid complexes with enhanced stability and biocompatibility, Journal of Controlled Release, 2011. 153 (3): p. 233-239).

Figure 3:
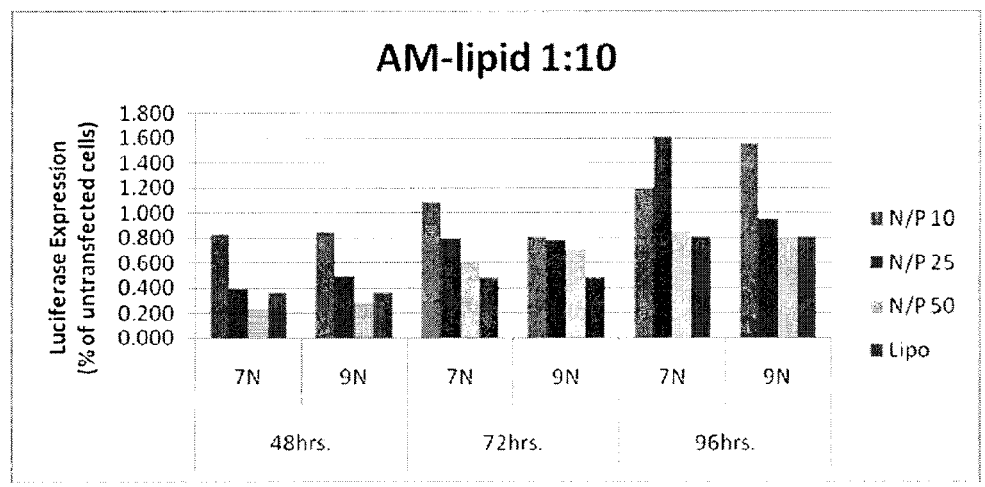
FIG. 3 shows the transfection efficacy of cationic AM-lipid (1:10) complexes at 48 hrs, 72 hrs, 96 hrs. For each complex depicted (7N (i.e. compound 7 nM), and 9N), the bar graphs from left to right are N/P=10, N/P=25, N/P=50, and lipofectamine, respectively.

The transfection efficacy of cationic AM-lipid complexes was evaluated by assays in U87 cell line using lipofectamine as positive control. The cationic AM:lipid weight ratios assayed were 0:1, 1:10, 1:5, 1:2, 1:1, 2:1, 5:1, 10:1 and 1:0 using previously reported methods, co-evaporation and post-addition (Harmon, A. M., et al., Preferential cellular uptake of amphiphilic macromolecule-lipid complexes with enhanced stability and biocompatibility, Journal of Controlled Release, 2011. 153 (3): p. 233-239). For the co-evaporation method, cationic AMs and lipid were co-dispensing aliquots in chloroform into glass vial and solvent removed by rotary evaporation. The remaining films were hydrated with 10 mM 4-(2-hydroxyethyl)-1-piperazineethanesulfonic acid (HEPES) buffer overnight at room temperature. The materials were then extruded 21 times through a mini-extruder to give unilamellar liposomes. For the post-addition method, cationic AM aliquots in 10 mM HEPES were added to extruded DOPE:DOTAP liposomes. The formed cationic AM lipid complexes were then complexed with anti-luciferase siRNA at N/P ratios of 10, 25, and 50. The transfection in the U87 MG cell line was performed at time points of 48, 72, and, 96 hrs using lipofectamine as the positive control. For cationic AM-lipid ratio of 1:10 shown in FIG. 3, 7N and 9N complexes with lipids showed comparable or slightly better efficacy than lipofectamine.

Certain embodiments of the invention are exemplified in the document "S. M. Sparks, C. L. Waite, A. M. Harmon, L. M. Nusblat, C. M. Roth, K. E. Uhrich, Efficient Intracellular siRNA Delivery by Ethyleneimine-Modified Amphiphilic Macromolecules. Macromol. Biosci., 2011, 11, 1192-1200" which is incorporated by reference in its entirety. Example 5 below describes some of these embodiments.

Example 5

Preparation and Physical/Biological Evaluation of Polymers 9N, 1N and 5N (the Compound Numbers Used in this Example Correspond to Those Shown in Scheme B Below)

Scheme B. Synthesis of 1N, 5N and 9N.

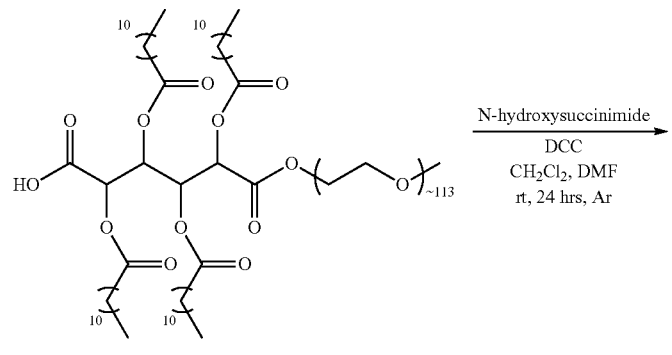

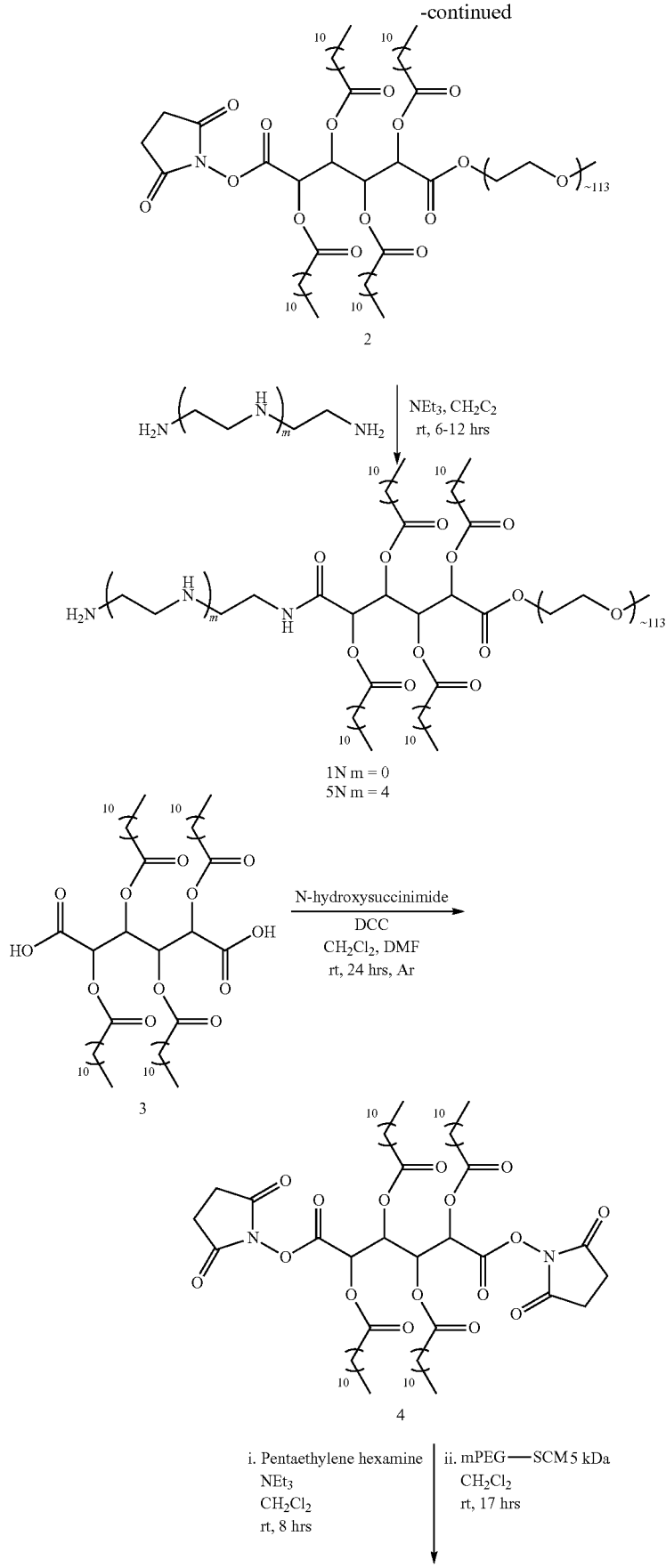

-continued

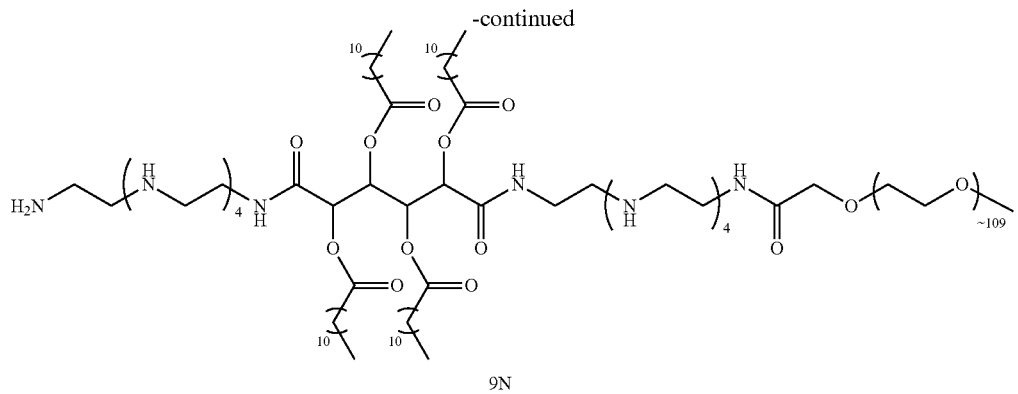

9N

Synthetic Materials:

Unless otherwise stated, solvents and reagents were purchased from Fisher Scientific (Pittsburgh, Pa.) and Sigma-Aldrich (St. Louis, Mo.) and used as received. Poly(ethylene glycol) kDa was purchased from Polysciences, Inc. (Warrington, Pa.) and dried by azeotropic distillation from toluene before use. N-hydroxysuccinimide (NHS)-functionalized PEG, Methoxy-PEG-succinimidyl carboxymethyl (MW 5 kDa) (mPEG-SCM). was purchased from Laysan Bio, Inc (Arab, Ala.) and used as received. Compounds 1, 2, and 3 were prepared as previously described (L. Tao, K. Uhrich, *Journal of Colloid and Interface Science* 2006, 298, 102; J. Djordjevic, M. Barch, K. Uhrich, *Pharmaceutical Research* 2005, 22, 24.)

Polymer Characterization Methods:

Proton nuclear magnetic resonance ($^1$H-NMR) spectra of the products were obtained using a Varian 400 MHz or 500 MHz spectrophotometer. Samples were dissolved in chloroform-d, with a few drops of dimethyl sulfoxide-$d_6$ if necessary, with tetramethylsilane as an internal reference. Molecular weights (Mw) and polydispersity indices (PDI) were determined using gel permeation chromatography (GPC) with respect to PEG (Sigma-Aldrich) on a Waters Stryagel® HR 3 THF column (7.8×300 mm). The Waters LC system (Milford, Mass.) was equipped with a 2414 refractive index detector, a 1515 isocratic HPLC pump, and 717plus autosampler. An IBM ThinkCentre computer with Waters Breeze Version 3.30 software installed was used for collection and processing of data. Samples were prepared at a concentration of 10 mg/mL in tetrahydrofuran, filtered using 0.45 μm pore size nylon or polytetrafluoroethylene syringe filters (Fisher Scientific) and placed in sample vials to be injected into the system. Melting points were determined by differential scanning calorimetry (DSC) on a TA DSC Q200. TA Universal Analysis 2000 software was used for data collection on a Dell Dimension 3000 computer. Samples (3-5 mg) were heated under dry nitrogen gas. Data were collected at heating and cooling rates of 10° C./min with a two-cycle minimum.

Polymer Synthesis:

1N:

Ethylenediamine (50 μL, 0.75 mmol) was dissolved in HPLC-grade $CH_2Cl_2$ (3 mL) and triethylamine (0.15 mL, 1.1 mmol). In a separate vessel, 2 (0.51 g, 0.085 mmol) was dissolved in HPLC-grade $CH_2Cl_2$ (9 mL) and subsequently added to the solution of ethylenediamine dropwise via syringe pump at a rate of 1.0 mL/hr. The reaction was stirred overnight (~18 hrs). The reaction solution was then diluted with $CH_2Cl_2$ and subsequently washed with 0.1 N HCl/brine (1×) and brine (2×). The combined aqueous portions were extracted with $CH_2Cl_2$ and the combined organics dried over $MgSO_4$, and concentrated to a yellow oil. The desired product was precipitated from the oil dissolved in $CH_2Cl_2$ (5 mL) by addition of 10-fold diethyl ether and cooling over dry ice for 1 hr. The solid was then collected by centrifugation at 3000 rpm for 5 min and the supernatant removed by decanting. The resulting white solid was dried under ambient atmosphere (12 hrs) and under high vacuum (12 hrs). Yield: 0.41 g, 80%. $^1$H-NMR (CDCl$_3$): δ 5.67 (m, 2H, CH), 5.14 (m, 2H, CH), 4.24 (m, 3H, CH$_2$), 3.60 (m, ~0.45 kH, CH$_2$O), 3.37 (s, 3H, OCH$_3$), 2.37 (m, 8H, CH$_2$), 2.29 (m, 4H, CH$_2$), 1.81 (b, 4H, CH$_2$), 1.60 (m, 8H, CH$_2$), 1.26 (m, 64H, CH$_2$), 0.87 (t, 12H, CH$_3$). $T_m$=58° C. GPC: $M_w$: 6.3 kDa; PDI: 1.1.

5N:

Pentaethylenehexamine (0.15 mL, 0.64 mmol) was dissolved in HPLC-grade $CH_2Cl_2$ (10 mL) and triethylamine (0.33 mL, 2.4 mmol). In a separate vessel, 2 (0.48 g, 0.079 mmol) was dissolved in HPLC-grade $CH_2Cl_2$ (10 mL) and subsequently added to the solution of ethylenediamine dropwise via syringe pump at a rate of 1.0 mL/hr. The reaction was stirred overnight (~17 hrs). The bright yellow reaction solution was diluted with $CH_2Cl_2$ and subsequently washed with 0.1 N HCl/brine (1×) and brine (2×). The combined aqueous portions were extracted with $CH_2Cl_2$ and the combined organics dried over $MgSO_4$, and concentrated to a cloudy yellow oil. The desired product was precipitated from the oil dissolved in $CH_2Cl_2$ (5 mL) by addition of 10-fold diethyl ether and cooling over dry ice for 1 hr. The solid was then collected by centrifugation at 3000 rpm for 5 min and the supernatant removed by decanting. The resulting white solid was dried under ambient atmosphere (12 hrs) and under high vacuum (12 hrs). Yield: 0.42 g, 86%. $^1$H-NMR (DMSO): δ 5.50 (m, 2H, CH), 5.11 (m, 2H, CH), 3.41 (m, ~0.45 kH, CH$_2$O), 3.24 (s, 3H, OCH$_3$), 2.89 (m, 13H, CH$_2$), 2.80 (bs, 2H, CH$_2$), 2.76 (bs, 7H, CH$_2$), 2.64 (bs, 6H, CH$_2$), 1.49 (m, 8H, CH$_2$), 1.24 (m, 64H, CH$_2$), 0.84 (t, 12H, CH$_3$). $T_m$=59° C. GPC: $M_w$: 6.4 kDa; PDI: 1.1.

4:

Product 3 (5.10 g, 5.43 mmol) and NHS (5.38 g, 46.8 mmol) were dissolved in anhydrous $CH_2Cl_2$ (100 mL) and anhydrous DMF (18 mL) under argon. Once a clear solution was obtained, N,N'-dicyclohexylcarbodiimide (17 mL, 17 mmol) was added and the reaction stirred at room temp under argon for 24 hours. The resulting solution with white suspension was stored at −4° C. overnight. The dicyclohexyl urea (DCU) byproduct was then removed by vacuum filtration and the filtrate washed with 0.1 N HCl and 50:50 brine/H$_2$O, dried over MgSO$_4$, and concentrated. The resulting white solid was then dissolved in a small amount of CH$_2$Cl$_2$ (5-10 mL) and stored at −4° C. for 2-3 hours. The resulting white suspension was filtered to remove residual DCU. The filtrate was then concentrated to dryness and the white solid dried under high vacuum overnight. Yield=4.5 g, 73%. $^1$H-NMR (CDCl$_3$): δ=5.96 (s, 2H, CH), 5.57 (s, 1H, CH), 2.81 (s, 8H, CH$_2$), 2.49 (m, 6H, CH$_2$), 2.37 (m, 2H, CH$_2$), 1.64 (m, 8H, CH$_2$), 1.27 (m, 64H, CH$_2$), 0.89 (t, 12H, CH$_3$).

9N:

Pentaethylenehexamine (0.05 mL, 0.2 mmol) was dissolved in CH$_2$Cl$_2$ (3 mL) and triethylamine (0.15 mL, 1.1 mmol). In a separate vessel, 4 (0.10 g, 0.090 mmol) was dissolved in HPLC-grade CH$_2$Cl$_2$ (3 mL) and subsequently added to the solution of ethylenediamine dropwise via syringe pump at a rate of 1.0 mL/hr. The reaction was stirred at room temperature a total of 8 hrs. mPEG-SCM (0.45 g, 0.090 mmol) dissolved in CH$_2$Cl$_2$ (7 mL) was then added to the yellow reaction solution dropwise via syringe pump at a rate of 1.0 mL/hr. The reaction was stirred at room temperature overnight (~17 hrs). The solvent was then removed from the reaction solution by rotary evaporation. The oil/solid was then redispersed in CH$_2$Cl$_2$ and filtered to remove the solid NHS-byproduct. The filtrate was concentrated to an oil and product precipitated from the oil dissolved in CH$_2$Cl$_2$ (5 mL) by addition of 10-fold diethyl ether. The solid was then collected by centrifugation at 3000 rpm for 5 min and the supernatant removed by decanting. The resulting white solid was washed with diethyl ether (1×) and dried under ambient atmosphere (12 hrs) and under high vacuum (12 hrs). Yield: 0.45 g, 87%. $^1$H-NMR (CDCl$_3$): δ 7.26 (s, 4H, CH), 3.69 (m, ~0.44 kH, CH$_2$O), 3.38 (s, 3H, OCH$_3$), 3.05 (bm, 15H, CH$_2$), 2.55 (bm, 16H, CH$_2$), 2.07 (bm, 40H, CH$_2$), 1.65 (bs, 7H, CH$_2$), 1.48 (t, 5H, CH$_2$), 1.26 (m, 37H, CH$_2$), 0.88 (t, 12H, CH$_3$). $T_m$=59° C. GPC: $M_w$: 5.5 kDa; PDI=1.1.

Size and Zeta Potential of AMs and AM/siRNA Complexes:

Dynamic light scattering (DLS) and zeta potential analyses were performed using a Malvern Instruments Zetasizer Nano ZS-90 instrument (Southboro, Mass.). DLS measurements were performed at a 900 scattering angle at 25° C. Size distributions by volume of measurements were collected in triplicate, averaged and reported. Zeta potential measurements were collected in triplicate, averaged and the Z-average charges reported. For all measurements, error bars represent peak widths of the average value.

Sample Preparation:

AMs alone: Polymer solutions at a concentration of 1.0 mg/mL were prepared using picopure water and filtered with a 0.45 M Nylon syringe filter (Fischer Scientific, Pittsburgh, Pa.).

AM/siRNA complexes: Complexes were prepared in picopure water at various nitrogen/phosphate (N/P) ratios. For size and zeta potential measurements, 2 mL of solutions containing AM/siRNA complexes were prepared at polymer concentrations sufficient for detection by the zetasizer instrument (1 mg/mL for 1 and 1N, and 2 mg/mL for 5N and 9N). Solutions were briefly vortexed and incubated for at least 60 min at room temperature to allow for complex formation prior to size and zeta potential analysis.

Figure 5:
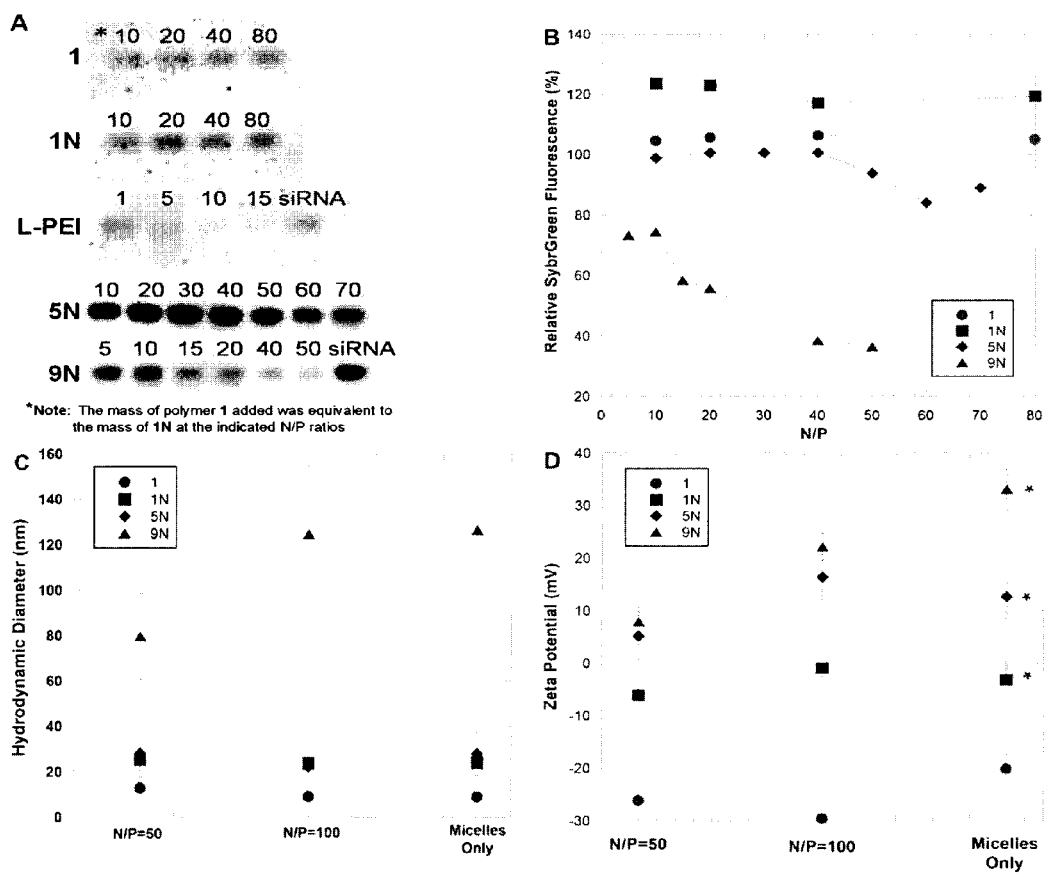
FIG. 5 shows the characterization of AM/siRNA complexes by gel electrophoresis (A and B), dynamic light scattering (C), and zeta potential (D). Relative SybrGreen fluorescence corresponds to unbound siRNA detected in an electrophoresis band normalized by a band of free siRNA (B). Images of gel electrophoresis bands are shown with the N/P ratio for each band denoted above the band, where the mass of polymer 1 added was equivalent to 1N at the indicated N/P ratios (A). Gel electrophoresis siRNA complexation studies were performed at least three times for each polymer, and one representative gel image and band quantification is shown here. The zeta potential measurements of each polymer were compared to each other at varying N/P ratios, and asterisks in D indicate polymers whose zeta potentials differed as a function of N/P ratio (p<0.05).

Gel Electrophoresis:

Polymer/siRNA (Dharmacon, Lafayette, Colo.) complexes were first prepared at the desired nitrogen to phosphorous (N/P) ratios by mixing solutions of polymers (stocks maintained in DI water) and siRNA in PBS (final siRNA concentration of 12.5 μg/mL). Since polymer 1 does not contain primary amines, the mass of polymer 1 added for the gel electrophoresis experiments was equivalent to the mass of polymer 1N added at the N/P ratios indicated in FIG. 5. Solutions were briefly vortexed, and incubated for 60 min at room temperature to allow for complex formation. Polymer/siRNA complexes were loaded into 1% agarose gels run in an electrophoresis chamber at 70 V for 40 minutes. Following electrophoresis, gels were stained with SYBR Green II RNA gel stain (Invitrogen, Carlsbad, Calif.) for 30 minutes prior to imaging on a Bio-Rad Molecular Imager FX (Bio-Rad Laboratories, Hercules, Calif.) to visualize unbound siRNA. The fluorescence intensities of bands were quantified using Quantity One Quantitation software (Bio-Rad Laboratories, Hercules, Calif.).

Cell Culture:

All cell culture products were obtained from Invitrogen (Carlsbad, Calif.). U87 MG cells (ATCC HTB-14) were maintained in DMEM medium supplemented with 10% fetal bovine serum (FBS), L-glutamine, and penicillin-streptomycin. A U87 cell line containing a stably integrated destabilized EGFP (d1EGFP) transgene (U87-GFP) was generated as described previously,[33] and was maintained under constant selective pressure by G418 (500 μg/mL), and the growth medium was supplemented with sodium pyruvate and nonessential amino acids. U87-Luc, a human glioblastoma cell line with constitutive expression of firefly luciferase, was generously provided by Dr. Xu-Li Wang (Department of Pharmaceutics and Pharmaceutical Chemistry, University of Utah). U87-Luc cells were maintained in minimal essential medium supplemented with 10% FBS, penicillin-streptomycin, and maintained under selective pressure by G418.

Cytotoxicity Assay:

U87 glioma cells were seeded into 96 well plates (Corning, Corning, N.Y.) at 10,000 cells per well in DMEM supplemented with 10% FBS and 1% penicillin-streptomycin and incubated overnight at 37° C., with 5% CO$_2$. The media was removed by aspiration and replaced with 200 μL aminated-AM or PEI dissolved in media at desired concentrations (n=4 per condition). Untreated control wells received media only. After 72 hours, cells were harvested by trypsinization (75 μL trypsin-EDTA followed with 75 μL complete media to neutralize trypsin) and 50 μL of staining solution (48:1:1 media: DMSO:Guava ViaCount Flex reagent (Guava Technologies, Hayward, Calif.) was added to each well. Cells were counted using a Guava EasyCyte Plus (Guava Technologies, Haywood Calif.) instrument with an original volume of 0.2 mL and a dilution factor of one.

siRNA Delivery Assay:

U87-Luc cells were plated at a density of 5000 cells/well in 96-well plates approximately hours prior to transfection. Immediately prior to transfection, polymer/siRNA complexes were prepared in 20 μL of PBS (N/P=50 for the AMs, and N/P=15 for linear PEI). Linear polyethyleneimine (Polysciences, Inc., Warrington, Pa.) commonly used polymeric transfection reagent, was used as a positive control. An irrelevant siRNA sequence not targeted against firefly luciferase was delivered as a negative control. The polyplexes were brought to a total volume of 100 μL in OptiMEM medium to obtain a final siRNA concentration of 100 nM. The serum-containing culture medium was aspirated from the cells, and each well treated with 100 μL of the polyplexes in OptiMEM medium. Each treatment was performed in triplicate. After a 4 hr incubation period, the transfection mixture was replaced with serum-containing growth medium and maintained under normal growth conditions until the cells were assayed for firefly luciferase expression 24 hours after the initial treatment.

For fluorescence imaging, a similar transfection protocol was performed on U87-GFP cells seeded onto an 8-well LabTek coverglass chamber (Nalge Nunc, Naperville, Ill.) at a density of 5000 cells/well. U87-GFP cells were treated with a Cy5-labeled siRNA to facilitate imaging of cellular localization of siRNA.

Fluorescence Microscopy:

Uptake of a fluorescently labeled siRNA (Dharmacon, Lafayette, Colo.) sequence into U87-GFP cells was evaluated using fluorescence microscopy. Imaging was performed 24 hours after siRNA transfection using an Olympus 1×81 model fluorescent microscope (Olympus, Center Valley, Pa.). Imaging was performed at 20× magnification. The following excitation and emission wavelengths were used: GFP (excitation=482 nm, emission=536 nm) and Cy5 siRNA (excitation=628 nm, emission=692 nm).

Luciferase Detection Assay:

Cells were prepared for firefly luciferase detection using the Luciferase Assay System (Promega, Madison, Wis.) according to the manufacturer's protocol. Firefly luciferase was quantified using The Reporter microplate luminometer (Turner Biosystems, Sunnyvale, Calif.). Following luciferase quantification, cell lysates were assayed for total protein content using the BCA Protein Assay kit (Pierce, Rockford, Ill.) according to the manufacturer's protocol.

Statistics:

Statistical comparisons for zeta potential measurements, luciferase silencing and polymer cytotoxicity were performed using a one-way ANOVA test with a Fisher's all-pairs post hoc comparison test.

Results and Discussion:

AMs (e.g. polymers) were modified with two different lengths of ethyleneimine chains to yield three polymer systems: ethylenediamine to yield 1N, or pentaethylenehexamine to yield 5N and 9N polymers. The polymers were synthesized as shown in Scheme B from the amine-specific N-hydroxysuccinimide (NHS)-activated polymer 1, which has been the focus of a previous publication (J. Djordjevic, L. Del Rosario, J. Wang, K. Uhrich, *Journal of Bioactive and Compatible Polymers* 2008, 23, 532; E. Chnari, J. Nikitczuk, J. Wang, K. Uhrich, P. Moghe, *Biomacromolecules* 2006, 7, 1796.)

The parent compound, 3, served as the basic building block for the polymer modifications. Specifically, the carboxylic acid on the mucic acid backbone was activated with N-hydroxysuccinimide to functionalize the polymers with linear ethyleneimines, systematically increasing the total number of amines in the final polymers from one, 1N, up to nine, 9N. For 1N and 5N, an excess of the diamines coupled with their slow addition to the polymer solution via syringe pump were utilized to control for the disubstitution of polymer to both primary amines. For 9N, a 2:1 molar ratio of compound 4 to pentaethylene hexamine coupled with the slow addition of 4 to the diamine via syringe pump were used to limit the formation of undesired oligomers. Subsequently, a 1:1 molar ratio of the NHS-PEG with respect to 4 coupled with its slow addition to the diaminated 4 via syringe pump were utilized to limit the coupling of PEG to both sides of the 4. For all aminated polymers, isolation of cationic AMs with amines conjugated to, rather than associated with, the polymer was insured by precipitation from diethyl ether; this process precipitates the AM products but not the ethyleneimine starting materials. Amine conjugation was further verified by $^1$H NMR spectroscopy. In addition to monitoring $^1$H NMR spectra for the disappearance of protons associated with the NHS activating group (~2.8 ppm), new peaks assigned to the ethyleneamine protons were observed resonating at 1.3 and 1.8 ppm for 1N and from 2.5-3.0 ppm for 5N and 9N. For all cationic AMs, the integrations of the $^1$H NMR are consistent with mono PEG substitution to produce the desired, cationic AMs. The molecular weights of the cationic AMs were determined by GPC relative to PEG standards. As shown in Table 1 below, 1N and 5N have similar molecular weights while the molecular weight of 9N is approximately 1 kDa less. This difference can be attributed to the use of different PEG starting materials from different vendors with varying peak molecular weights. In addition, due to the incorporation of amines between the hydrophobic and hydrophilic component in the structure of 9N, the polymer may associate more with the column than the other cationic polymers, thereby making the molecular weight appear lower than it actually is. For all cationic AMs, the absence of a high molecular weight peak in the GPC corresponding to ~10 kDa suggests there was little-to-no PEG di-substitution in any of the resulting polymers.

TABLE 1

Molecular weights, poydispersity indices (PDI), and melting temperature ($T_m$) ethyleneimine-modified AMs

| Cationic AM | Mw (kDa) | PDI | $T_m$ (° C.) |
|---|---|---|---|
| 1N | 6.3 | 1.1 | 58 |
| 5N | 6.4 | 1.1 | 59 |
| 9N | 5.5 | 1.1 | 59 |

Figure 4:
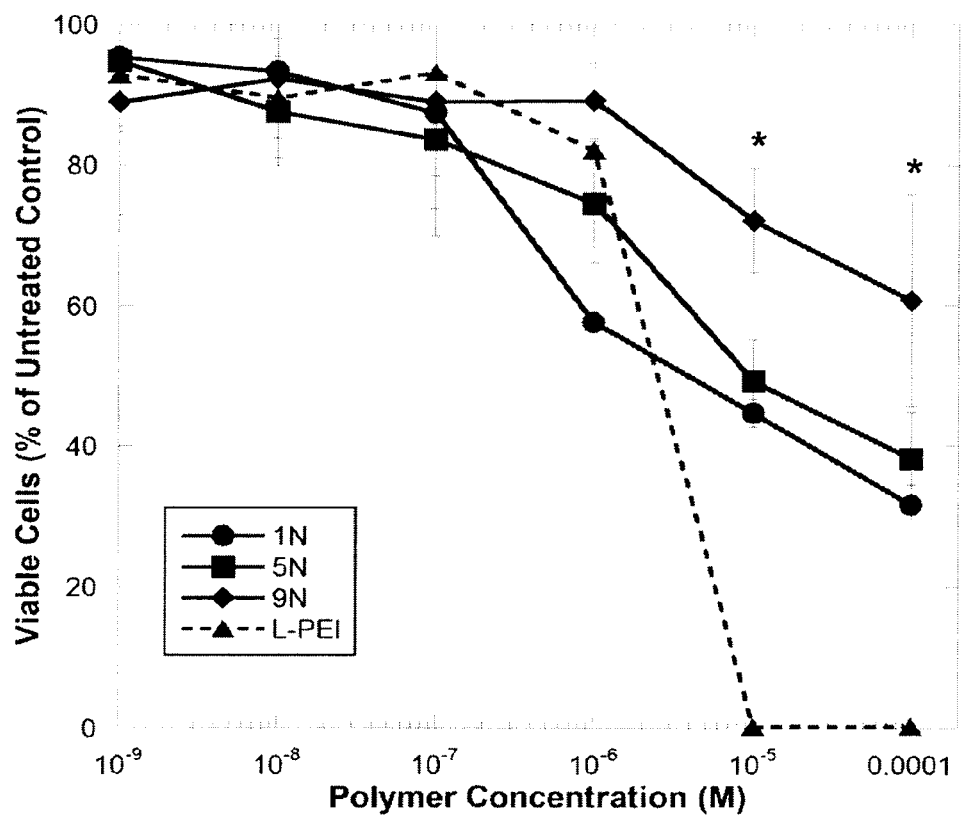
FIG. 4 shows the cytotoxicity of cationic-AMs and L-PEI to U87 glioma cells after 72 hours of exposure. Data represent mean±standard deviation (n=4). Astericks represent concentrations at which cationic-AMs elicited a significantly lower cytotoxicity than L-PEI (p<0.05).

The toxicity of the aminated-AMs compared to linear PEI 25 kDa (L-PEI) was assessed in U87 glioma cells. A dose response curve was generated for all samples by counting viable cells remaining after a 72-hour exposure to the polymers (FIG. 4). A significant decrease in cytotoxicity ($p<0.05$) was observed for all AMs compared to L-PEI at the highest concentrations tested ($10^{-5}$ and $10^{-4}$ M). Interestingly, when comparing the AMs, the 9N material exhibited the lowest cytotoxicity compared to the AMs containing fewer amine groups. One possible explanation for this observation is that the surface charge density of the 9N micelles is lower as their hydrodynamic diameter (shown in FIG. 5c) has increased by a factor of approximately five and, therefore, their area is increased by a factor of about 25 compared to the 1N and 5N micelles.

The ability of cationic AMs to complex anionic siRNA was evaluated using gel electrophoresis. Complexes were formed at a range of N/P ratios and run on an electrophoresis gel to separate un-complexed siRNA from the AM/siRNA complexes. The decrease in fluorescence intensity of the band corresponding to un-complexed siRNA verifies the siRNA complexation efficiency of the cationic AMs. Polymers containing zero or one cationic amine group (i.e., 1 and 1N) displayed no complexation of siRNA at charge ratios tested up to nitrogen/phosphorus (N/P) 80 (FIG. 5b). By increasing the number of amine groups to five (5N), a modest extent of siRNA complexation (approximately 20%) was observed at N/P ratios of 60 and higher. Significantly improved siRNA complexation efficiency was observed by using the AM containing nine amine groups, 9N, where most of the siRNA was encapsulated by N/P=50. The ability of AMs to complex siRNA was compared to L-PEI, where nearly complete siRNA complexation was observed by gel electrophoresis at N/P≥15. Hence, for subsequent physical and biological characterization studies, AM/siRNA complexes were formed at N/P≥50.

All cationic AMs formed micelles in the nanoscale size range as determined by dynamic light scattering (FIG. 5c). 1N and 5N formed micelles of approximately the same size as polymer, 1, while micelles formed from 9N were much larger (~125 nm), presumably due to charge repulsion of the highly cationic ethyleneimine units. Once complexed with siRNA (FIG. 5c, N/P=50 and 100), all cationic AMs maintained the nanoscale size of the AMs alone. Self-assembled polymeric micelles are known to have stable sizes that are dictated primarily by the architecture of the amphiphilic polymer segments (K. Kataoka, A. Harada, Y. Nagasaki, *Advanced Drug Delivery Review* 2001, 47, 113.) Especially at high N/P ratios, the size of polymer micelles often remains unchanged in the presence of nucleic acids as the presence of relatively small amounts of siRNA does not change the properties of the stable polymer micelles (K. Kataoka, A. Harada, Y. Nagasaki, *Advanced Drug Delivery Review* 2001, 47, 113; S. Matsumoto, R. Christie, N. Nishiyama, K. Miyata, A. Ishii, M. Oba, H. Koyama, Y. Yamasaki, K. Kataoka, *Biomacromolecules* 2009, 10, 119). Maintaining sizes of less than ~100 nm is desirable for improved circulation time, passive tumor targeting by the enhanced permeation and retention (EPR) effect, and optimal cellular uptake (L. Brannon-Peppas, J. O. Blanchette, *Advance Drug Delivery Reviews* 2004, 56, 1649; M. E. Davis, Z. Chen, D. M. Shin, *Nature Reviews Druge Discovery* 2008, 7, 771).

Successful conjugation of the amines was shown by the disappearance of N-hydroxysuccinimide in the $^1$H NMR as well as the increase in the zeta potential from negative (for polymer 1), to less negative (polymer 1N), and positive (polymers 5N and 9N), as shown in FIG. 5d (micelles only). The zeta potential increased with increasing ethyleneimine length, further indicating the successful incorporation of amine groups. When siRNA was complexed with the cationic AMs at N/P ratios of 50 and 100, the zeta potentials for the aminated polymers 5N and 9N significantly changed compared to the native polymer in the absence of siRNA (p<0.05). Specifically, at N/P 50, the zeta potentials for complexes of siRNA and 5N decreased from 12.7 mV of the 5N alone to 5.3 mV when complexed with siRNA. Likewise, the zeta potential of 9N decreased from 33.1 mV alone to 7.89 mV when complexed with siRNA. The zeta potentials for both AMs increased at N/P 100—back to that for the vehicle alone for 5N but only to 22.2 mV for 9N. This data suggests that 9N complexed most efficiently with siRNA at the N/P ratios evaluated in this study, as the decrease in zeta potential is a result of charge neutralization when the negatively charged siRNA complexes with the cationic AMs. These results are in agreement with the gel electrophoresis data. Based on the physical characterization of AM/siRNA complexes by gel electrophoresis, dynamic light scattering, and zeta potential, 9N was expected to be the most effective siRNA delivery vehicle.

Figure 6:
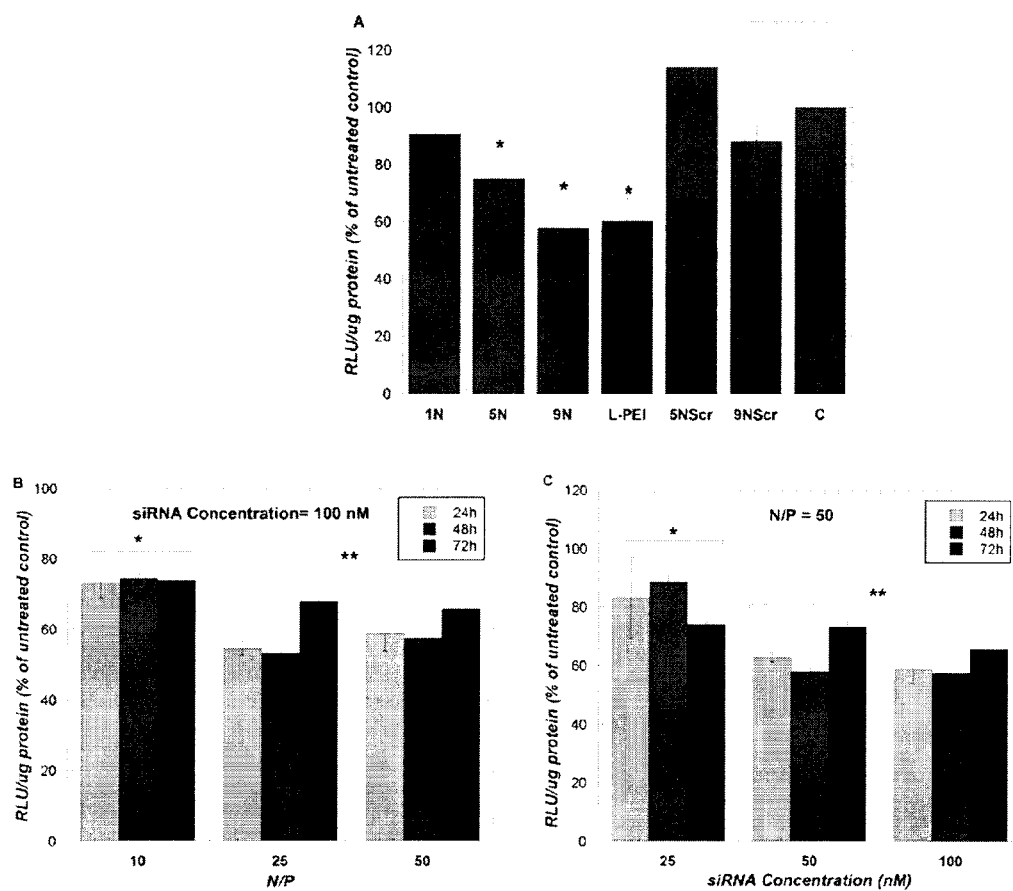
FIG. 6 shows luciferase silencing in U87-Luc cells 24 hours post-transfection (A). L-PEI was used at N/P=15. The samples 5NScr and 9NScr indicate treatments with a scrambled siRNA sequence. Time-course and dose titrations were performed of 9N/siRNA complexes to U87-Luc cells (B and C). Data represent mean±standard deviation (n=3). Asterisks indicate treatments that elicited statistically significant luciferase silencing compared to the untreated control, B (A) or treatments that elicited statistically different luciferase silencing compared to the other treatment groups in the experiment (B and C) (p<0.05).

The ability of AMs to facilitate cellular delivery of siRNA and elicit silencing of the reporter gene, firefly luciferase, in U87 cells was evaluated. Polyplexes of AMs and anti-luciferase siRNA were formed (siRNA concentration: 100 nM, N/P=50, AM concentration: ~$10^{-5}$ M) and delivered to U87-Luc cells which were subsequently assayed for luciferase expression. To visually evaluate the cellular uptake of siRNA, a fluorescently labeled siRNA sequence was delivered separately to U87-GFP cells which were then imaged using fluorescent microscopy Significant luciferase silencing (p<0.05) was observed using the AMs containing five or nine amines (5N and 9N), but not observed using the AMs containing just one amine group (1N) (FIG. 6A). A similar luciferase silencing response was observed between the 9N and L-PEI, a widely-studied polymeric system for nucleic acid delivery (FIG. 6A). Delivering a scrambled siRNA sequence did not elicit luciferase silencing, demonstrating that the AMs alone do not induce off-target silencing effects.

To study the dynamics and dose-dependence of luciferase silencing by 9N, siRNA transfection experiments were performed at various time points, polymer concentrations (FIG. 6B) and siRNA concentrations (FIG. 6C). The minimum N/P ratio required for a maximum luciferase silencing response was N/P=25 (siRNA concentration: 100 nM, AM concentration: $1.2 \times 10^{-5}$ µM), (FIG. 6B), and the minimum siRNA concentration required for optimal silencing response was 50 nM (FIG. 6C).

Studying the dose response and dynamics of siRNA delivery by AMs provides insights into the mechanisms governing siRNA delivery by these novel molecules. The results suggest that using polymer 9N at N/P>25 may not be as biologically beneficial as similar extents of gene silencing were observed using 9N at N/P=25 and N/P=50. One goal in polymeric delivery systems is to identify the lowest possible polymer concentration that can achieve optimal siRNA delivery, as having excessively high polymer concentrations can elicit undesirable cytotoxicity and may result in insolubility of polymers in aqueous media. Further, it was observed that using siRNA concentrations of 50 nM was sufficient to achieve maximal luciferase gene silencing with 9N. Possibly, having siRNA in excess of the minimum effective concentrations is unnecessary as the number of target mRNAs present in the cell is limited; the cells are sufficiently targeted by siRNA at 50 nM.

Trends in siRNA silencing as a function of time, where maximum siRNA silencing was observed at 48 hours, and decreased after 72 hours were also observed. This trend in gene silencing dynamics is consistent with previous work evaluating the gene silencing dynamics of antisense oligonucleotides delivered by branched PEIs where the silencing of green fluorescent protein (GFP) became less pronounced after 24 hours (S. Sundaram, L. K. Lee, C. M. Roth, *Nucleic Acids Res* 2007, 35, 439690). This decrease in gene silencing activity after 48 hours may be attributed to intracellular degradation of siRNA molecules by nucleases over time.

The trends observed in the quantitative luciferase silencing assay differed somewhat from the qualitative observations of cellular association of a fluorescently labeled siRNA sequence into U87GFP cells. It appeared that 9N delivered more siRNA to the cells than L-PEI in the fluorescent images, however, this trend was not observed in the luciferase silencing assay where both 9N and L-PEI elicited similar extents of luciferase silencing. This observation may suggest that while 9N may be capable of delivering siRNA to cells, other intracellular barriers such as siRNA unpackaging or endosomal escape may be affecting gene silencing activity by 9N.

By increasing the number of secondary amines from one up to nine (i.e., from 1N to 9N, respectively), increased zeta potential and stable complexation with siRNA was achieved. All cationic AMs were less cytotoxic to U87 cells than L-PEI at polymer concentrations of 10 µM or greater.

Example 6

Cationic Amphiphilic Macromolecule (CAM)-Lipid Complexes

Small interfering ribonucleic acid (siRNA) has been viewed widely as a promising gene-based therapeutic approach for many diseases since the discovery of RNA interference (RNAi) by Fire et al. (Nature, 391 (1998) 806-811). Due to the anionic nature of siRNA and the presence of RNases in the bloodstream, delivery of naked siRNA is limited by inadequate cellular uptake and poor stability under physiological conditions. Therefore, improved efficiency of siRNA delivery vehicles is necessary. While viral delivery systems have demonstrated high transfection efficacies, typically only one copy of siRNA is encoded per virus. Furthermore, viruses are limited by safety concerns. To circumvent these challenges, numerous non-viral delivery systems, including cationic polymer-based and lipid-based systems (Wong et al., Progress in Polymer Science, 32 (2007) 799-837; Zhang et al., Journal of Controlled Release, 123 (2007) 1-10; and Buyens et al., J Control Release, 158 (2012) 362-370), cell-penetrating peptides (Endoh et al., Advanced Drug Delivery Reviews, 61 (2009) 704-709; and Ezzat et al., J Control Release, 162 (2012) 1-8), and chemically modified siRNAs (Jung et al., Journal of Controlled Release, 144 (2010) 306-313; and Jeong et al., Bioconjugate Chemistry, 20 (2009) 5-14), have been developed. To date, only a limited number of non-viral siRNA delivery systems have reached clinical trials due to low delivery efficiencies in vivo and high cytotoxicities (Burnett et al., Biotechnol J, 6 (2011) 1130-1146). Effective non-viral siRNA delivery vehicles with minimal cytotoxicity are thus still needed.

Cationic systems involving polymers and lipids have been developed for siRNA delivery as they prevent siRNA degradation, allow siRNA endosomal escape, and silence the target mRNA (Creusat et al., Bioconjug Chem, 21 (2010) 994-1002; and Huang et al., J Control Release, 152 Suppl 1 (2011) e143-145). Yet, these cationic systems have yet to overcome cytotoxicity, instability in the presence of serum, and low silencing efficiency compared to the existing "gold standard", Lipofectamine, for intracellular siRNA delivery in vitro. To address these issues, a mixed system containing cationic amphiphilic macromolecules (CAMs) and lipid was developed. CAMs are comprised of hydrophobic acyl chains and hydrophilic poly(ethylene glycol) (PEG). Within aqueous media, CAMs can self-assemble into micelles to present the PEG shell which increases the system's circulation time in the bloodstream (Gao et al., International Journal of Nanomedicine, (2011) 1017). Two species of CAMs, differing by the number of amine groups in their backbone (Scheme C, 7Nb and 9Nb), were prepared previously and were shown to exhibit moderate gene-silencing efficacy with low cytotoxicity in vitro (Sparks et al., Macromol Biosci, 11 (2011) 1192-1200). Thus, CAMs represent a promising delivery platform due to their self-assembly, biocompatibility, and surface chemistry modification ability.

While CAMs alone are promising siRNA delivery systems, a greater gene silencing efficiency may be desirable for certain practical applications. Cationic lipids are the most commonly used transfection agents for nucleic acid delivery due to their low cytotoxicity. As polymer delivery systems are limited by their high cytotoxicity in vivo, it is proposed herein that incorporating lipids will improve this siRNA delivery system. Furthermore, given the instability of lipid systems in the bloodstream, blending CAM with lipids could prevent lipid aggregation caused by serum proteins because of the PEG component in the CAM. A mixed lipid system consisting of 1,2-dioleoyl-sn-glycero-3-phosphoethanolamine (DOPE) and 1,2-dioleoyl-3-trimethylammonium-propane (DOTAP) (Scheme C) with weight ratio of 1:1 was designed to create a CAM-lipid complex system. DOPE was chosen for its ability to destabilize endosomal membranes and enhance siRNA release (Zhang et al., Int J Pharm, 390 (2010) 198-207), while DOTAP was chosen for its high transfection efficiency and lower cytotoxicity due to its cationic and lipidic features (Martino et al., J Biomed Biotechnol, 2009 (2009) 410260). Complexes with different CAM-lipid weight ratios were formulated to discern a CAM-lipid system with enhanced transfection efficacy as well as increased stability under physiological conditions. CAM-lipid complexes with various CAM-to-lipid weight ratios were prepared according to a previously reported method (Harmon et al., Journal of Controlled Release, 153 (2011) 233-239). Dynamic light scattering (DLS) and transmission electron microscopy (TEM) were used to measure the sizes and morphologies of CAM-lipid complexes. Zeta potentials were also obtained to verify the cationic surface charge, which is critical for electrostatic interactions between siRNA and CAM-lipid complexes. Transfection efficiency and endosomal escape of CAM-lipid complexes were evaluated using an in vitro assay with a human primary glioblastoma cell line (U87) and anti-Luciferase siRNA or Cy5-scrambled siRNA. The studies herein demonstrated that CAM-lipid complexes were developed as an efficient intracellular siRNA delivery system.

Scheme C. Structure of CAMs (7Nb and 9Nb) (top), DOPE (middle), and DOTAP (bottom)

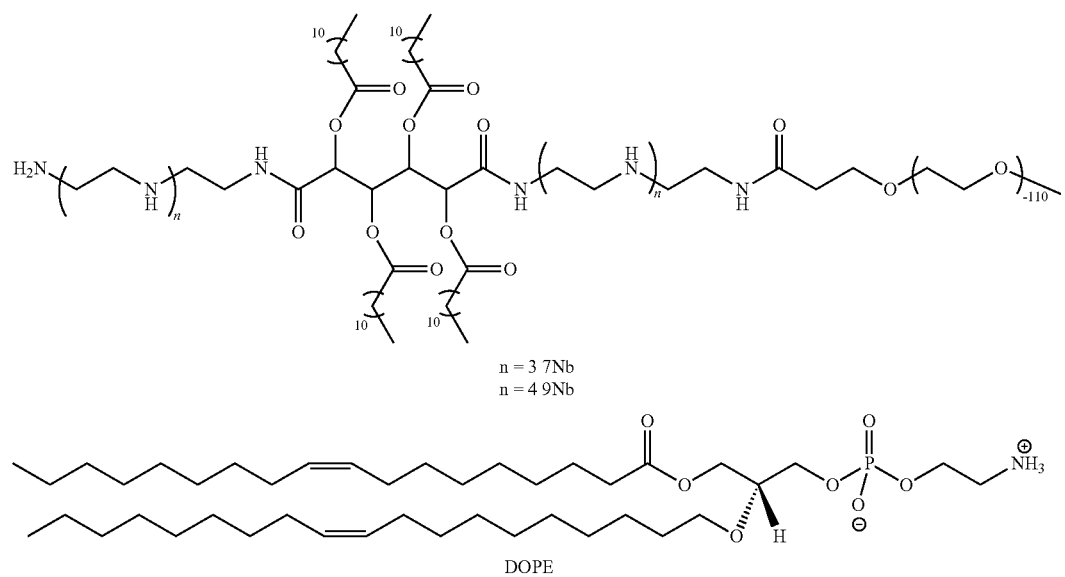

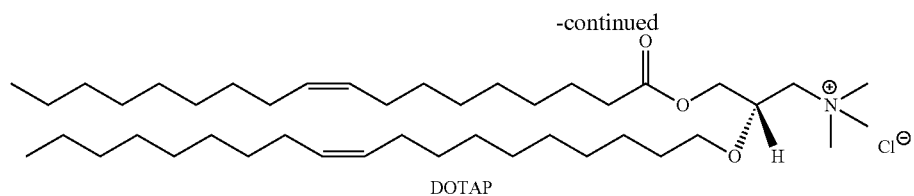
DOTAP

Preparation of 7Nb and 9Nb

Compounds 7Nb and 9Nb were prepared as described below.

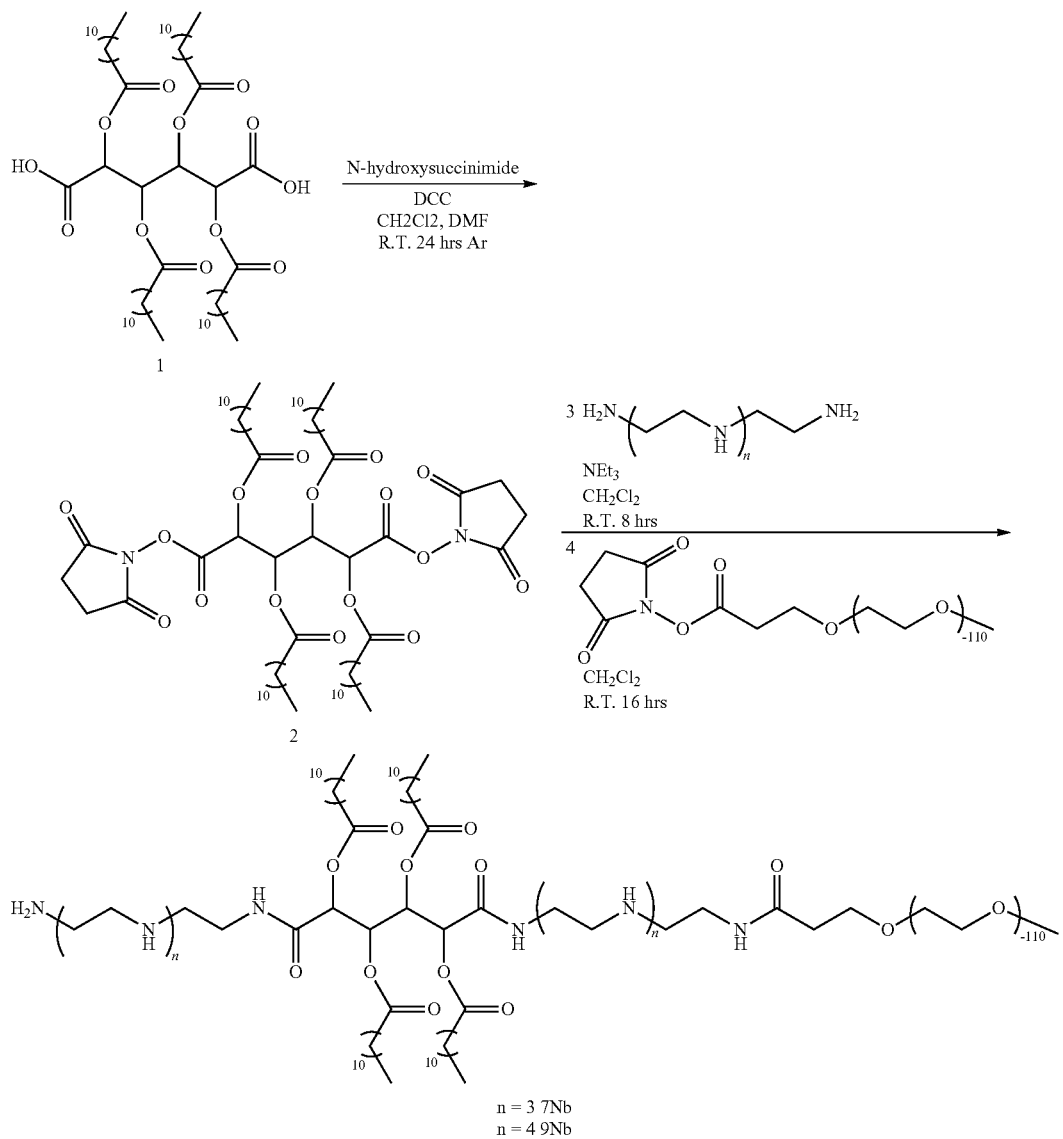

n = 3 7Nb
n = 4 9Nb

Synthesis of Compound 2:

Compound 1 (5.10 g, 5.43 mmol) and N-hydroxysuccinimide (5.38 g, 46.8 mmol) were dissolved in anhydrous $CH_2Cl_2$ (100 mL) and anhydrous DMF (18 mL) under argon. Once a clear solution was obtained, N,N'-dicyclohexylcarbodiimide (17 mL, 17 mmol) was added and the reaction stirred at room temp under argon for 24 hours. The resulting solution with white suspension was stored at −4° C. overnight. The dicyclohexyl urea (DCU) byproduct was then removed by vacuum filtration and the filtrate washed with 0.1 NHC and 50:50 brine/H2O, dried over MgSO4, and concentrated. The resulting white solid was then dissolved in a small amount of $CH_2Cl_2$ (5-10 mL) and stored at −4° C. for 2-3 hours. The resulting white suspension was filtered to remove residual DCU. The filtrate was then concentrated to dryness and the white solid dried under high vacuum overnight.

Synthesis of 7Nb (9Nb):

Tetraethylenepentamine (For 9Nb, use Pentaethylenehexamine) (0.05 mL, 0.2 mmol) was dissolved in $CH_2Cl_2$ (3 mL) and triethylamine (0.15 mL, 1.1 mmol). In a separate vessel, 2 (0.10 g, 0.090 mmol) was dissolved in HPLC-grade $CH_2Cl_2$ (3 mL) and subsequently added to the solution of tetraethylenepentamine (For 9N, use Pentaethylenehexamine) dropwise via syringe pump at a rate of 1.0 mL/hr. The reaction was stirred at room temperature a total of 8 hrs. mPEG-SCM (compound 4) (0.45 g, 0.090 mmol) dissolved in $CH_2Cl_2$ (7 mL) was then added to the yellow reaction solution dropwise via syringe pump at a rate of 1.0 mL/hr. The reaction was stirred at room temperature overnight (~17 hrs). The solvent was then removed from the reaction solution by rotary evaporation. The oil/solid was then redispersed in $CH_2Cl_2$ and filtered to remove the solid NHS-byproduct. The filtrate was concentrated to an oil and product precipitated from the oil dissolved in $CH_2Cl_2$ (5 mL) by addition of 10-fold diethyl ether. The solid was then collected by centrifugation at 3000 rpm for 5 min and the supernatant removed by decanting. The resulting white solid was washed with diethyl ether (1×) and dried under ambient atmosphere (12 hrs) and under high vacuum (12 hrs).

Intermediate Compound 1 was synthesize as described by L. Tian, L. Yam, N. Zhou, H. Tat, K. Uhrich, *Macromolecules* 2004, 37, 538.

Materials and Methods

Materials.

DOPE and DOTAP were purchased from Avanti Polar Lipid (Alabaster, Ala.). All cell culture media and Lipofectamine were purchased from Invitrogen (Carlsbad, Calif.). The Luciferase assay kit and BCA protein assay kit were purchased from Promega (Madison, Wis.). U87-LUC, a human primary glioblastoma cell line with constitutively active expression of firefly luciferase, was generously provided by Dr. Xu-Li Wang (Department of Pharmaceutics and Pharmaceutical Chemistry, University of Utah). All other reagents were purchased from Sigma-Aldrich (St. Louis, Mo.) and used as received without further purification.

CAM-Lipid Complex Preparation.

Complexes of various CAM-lipid ratios were prepared by a co-evaporation technique previously described (Harmon et al., Journal of Controlled Release, 153 (2011) 233-239). The lipid component was comprised of a 1/1 (mass/mass) mixture of DOPE and DOTAP. The resulting films were hydrated with 10 mM 4-(2-hydroxyethyl)-1-piperazineethanesulfonic acid (HEPES) overnight at room temperature. The complex solutions were then extruded 21 times through a mini-extruder to give unilamellar structures.

Electrophoretic Mobility Shift Assay.

CAM-lipid/siRNA complexes were prepared as previously described for CAM/siRNA complexes (Sparks et al., Macromol Biosci, 11 (2011) 1192-1200). Solutions were briefly vortexed and incubated for 60 m at room temperature to allow for complex formation. Prior to electrophoresis, 2 µL of 100× BlueJuice gel loading buffer was added to each sample. Gel electrophoresis was performed using 0.8% agarose E-gels containing ethidium bromide for DNA visualization and a PowerBase electrophoretic chamber (Invitrogen). Gels were imaged using BioDoc-It Imaging System (UVP).

Transmission Electron Microscopy.

A drop of CAM-lipid complex solution (0.05 mg/mL) with or without siRNA and a drop of uranyl acetate (0.5 mg/mL) were both dropped on a carbon film-coated copper grid. Excess solution was removed by tapping the edge of grid with filter paper. The grid was then dried for 30 min in a desiccator at room temperature. Images were taken on a TEM-Topcon 002B.

CAM-Lipid Size and Zeta Potential.

CAM-lipid complexes (1 mg/mL in HEPES) with or without siRNA were analyzed using a NanoZS90 instrument (Malvern Instruments, UK) at room temperature. Each sample was run three separate times with 20 measurements per run to obtain the size and zeta potential.

Cell Culture.

U87 and U87-LUC cells were maintained in DMEM medium supplemented with 10% fetal bovine serum (FBS) and 1% penicillin/streptomycin. Cells were incubated at 37° C. in a 5% $CO_2$ incubator. For the U87-LUC cell line, which stably expresses luciferase, expression was maintained by culturing in media containing G418.

Cytotoxicity.

The cytotoxicity of CAM-lipid complex with varying fractions of lipid and CAM was assessed with an MTS assay in U87 cells. Cells were seeded in 96-well plates for 24 h. Following transfection with the various CAM-lipids for 4 h, cells were washed 3 times and cultured in serum-containing media. After 48 h, an MTS assay was performed and the absorbance at 450 nm was measured by a DTX880 Multimode Detector microplate reader (Beckman Coulter). Cell viability was normalized to that of U87 cells with HEPES treatment.

Intracellular Trafficking.

U87 cells were seeded in 24-well plates at 70% confluency and allowed to adhere overnight. After 4 h or 24 h of incubation with Cy5-siRNA (scrambled) and 1:10 CAM-lipids, 10:1 CAM-lipids, or Lipofectamine control, U87 cells were washed twice with HEPES and stained with LysoTracker Red (Molecular Probes). After fixation in 4% paraformaldehyde for 15 min and counterstaining with 4',6-diamidino-2-phenylindole (DAPI), images were taken on an IX81 motorized inverted confocal microscope (Olympus) to view siRNA localization within the cells.

siRNA Delivery Assay.

U87 cells were plated at a density of 5000 cells/well in 96-well plates approximately 20 h prior to transfection. Immediately prior to transfection, CAM-lipid/siRNA complexes were prepared in 20 µL of HEPES (N/P=50). Lipofectamine was used as a positive control. A 100 nM siRNA solution was used, while CAM-lipid stock solutions were prepared at 20 nM. The CAM-lipid/siRNA complexes were brought to a total volume of 100 µL in OptiMEM medium. The serum-containing culture medium was aspirated from the cells and each well treated with 100 µL of CAM-lipid/siRNA complexes in OptiMEM medium. After a 4 h incubation period, cells were washed 3 times with HEPES and the transfection mixture was replaced with a serum-containing growth medium and maintained under normal growth conditions. After 48 h, the cells were assayed for firefly luciferase expression using a luminometer (Turner Biosystems) which was normalized to total protein expression using a BCA assay kit (Promega).

Statistical Analysis.

Statistical analyses were carried out using a Student's t-test. The significance criteria assumed a 95% confidence level ($P<0.05$). Standard error of the mean is reported in the form of error bars on the graphs of the final data.

Results and Discussion

Figure 7:
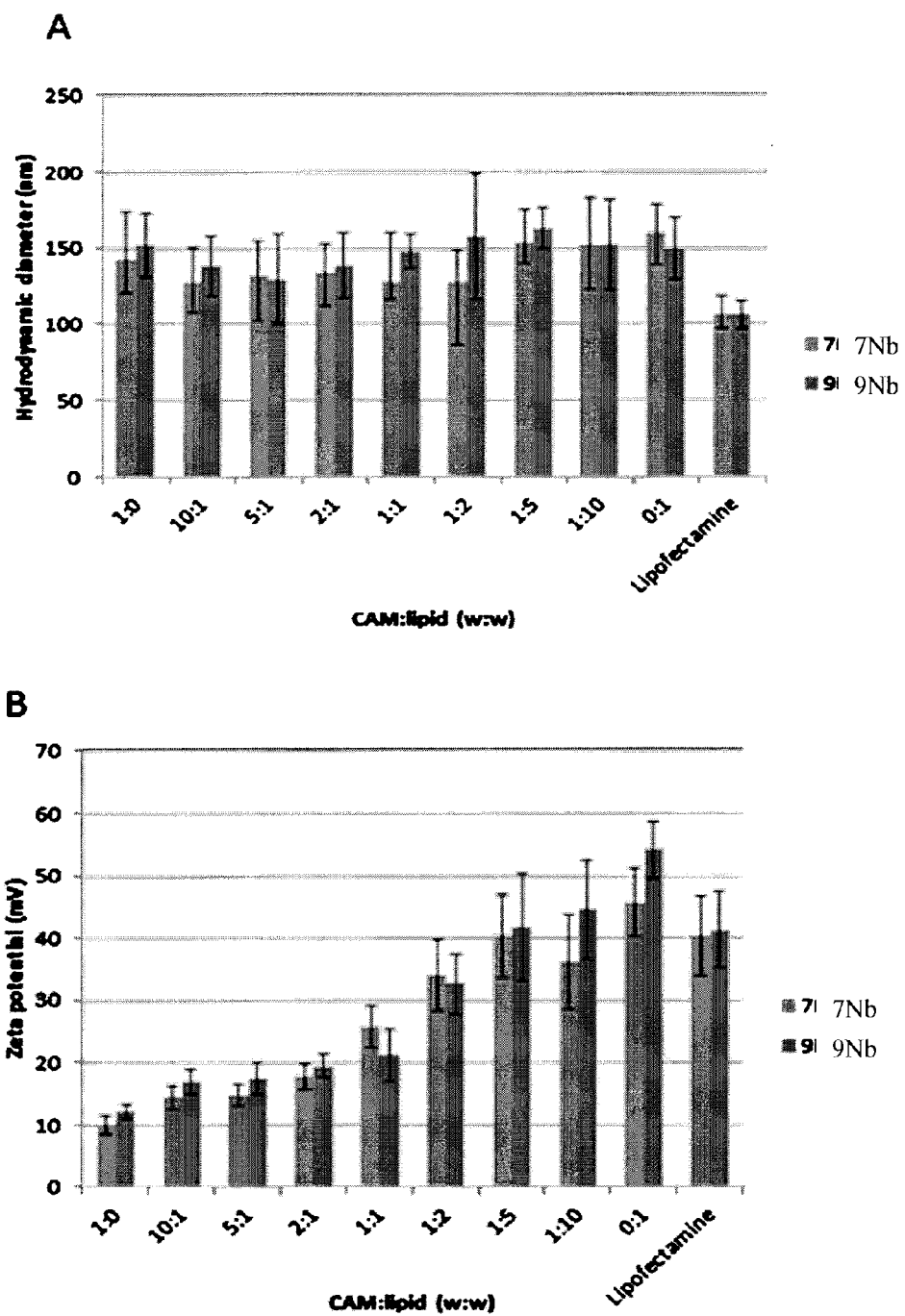
FIG. 7. (A): Hydrodynamic radii of CAM-lipid complexes in HEPES (10 mM, pH=7.4) buffer with different weight ratios using DLS (the 7Nb-lipid complex is represented by the light grey bar on the left and 9Nb-lipid complex is represented by the dark grey bar on the right for each ratio pairing). (B): Zeta potentials of CAM-lipid complexes in HEPES (10 mM, pH=7.4) with different weight ratios (the 7Nb-lipid complex is represented by the light grey bar on the left and 9Nb-lipid complex is represented by the dark grey bar on the right for each ratio pairing). Lipofectamine was used as control. Data represent mean±standard deviation (n=3). (C): electrophoresis gel, lane 1-9 correspond to 9Nb:lipid weight ratios of 1:0, 10:1, 5:1, 2:1, 1:1, 1:2, 1:5, 1:10, 0:1 at N/P ratio of 50, lane 10 is Lipofectamine, lane 11 is siRNA alone. (D): TEM image of CAM (9N_b)-lipid with 1:1 weight ratio.
Figure 7:
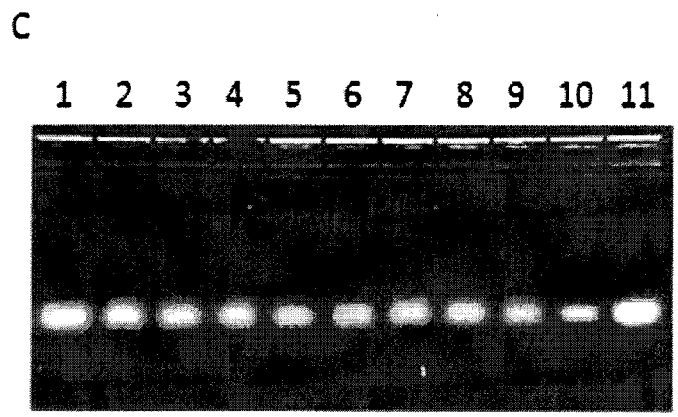
Figure 7:
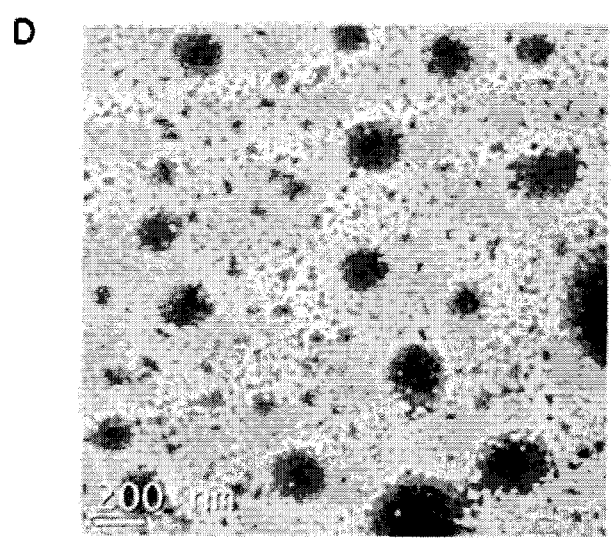

After CAM-lipid complexes were formulated using the previously reported method (Harmon et al., Journal of Controlled Release, 153 (2011) 233-239), their sizes were characterized using DLS. As shown in FIG. 7A, CAM-lipid complexes for all compositions were between 130 to 160 nm in diameter, which is within the range generally considered ideal for both cellular uptake and systemic circulation (Convertine et al., Biomacromolecules, (2010); Nuhn et al., ACS Nano, 6 (2012) 2198-2214; and Wang et al., J Control Release, 134 (2009) 207-213). CAM-lipid complex zeta potentials varied monotonically between that for CAM alone (~10 mV) and that for lipid alone (~50 mV) (FIG. 7B). Gel electrophoresis was used to monitor siRNA binding to the CAM-lipid complexes. As was the case for CAMs alone (Sparks et al., Macromol Biosci, 11 (2011) 1192-1200), it was found that an N/P ratio of 50 was necessary for efficient siRNA complexation with CAM:lipid mixtures. As shown in FIG. 7C, at an N/P ratio of 50, only a minor fraction of siRNA migrated on the gel, indicating complexation of siRNA to 9Nb-lipid, for all CAM:lipid ratios. Similar results were observed when 7Nb-lipid was used (data not shown). FIG. 7D shows a TEM image of 9Nb-lipid complex with weight ratio of 1:1. The size measured by TEM correlated with the DLS observations, and a spherical morphology was also demonstrated. These results indicated that the CAM-lipid/siRNA complex diameters remained at approximately 100-200 nm, suggesting that the size of the nanocomplex is not affected significantly by the presence of siRNA. Despite this decrease, all of the CAM-lipid/siRNA complexes maintained a net cationic charge.

Figure 8:
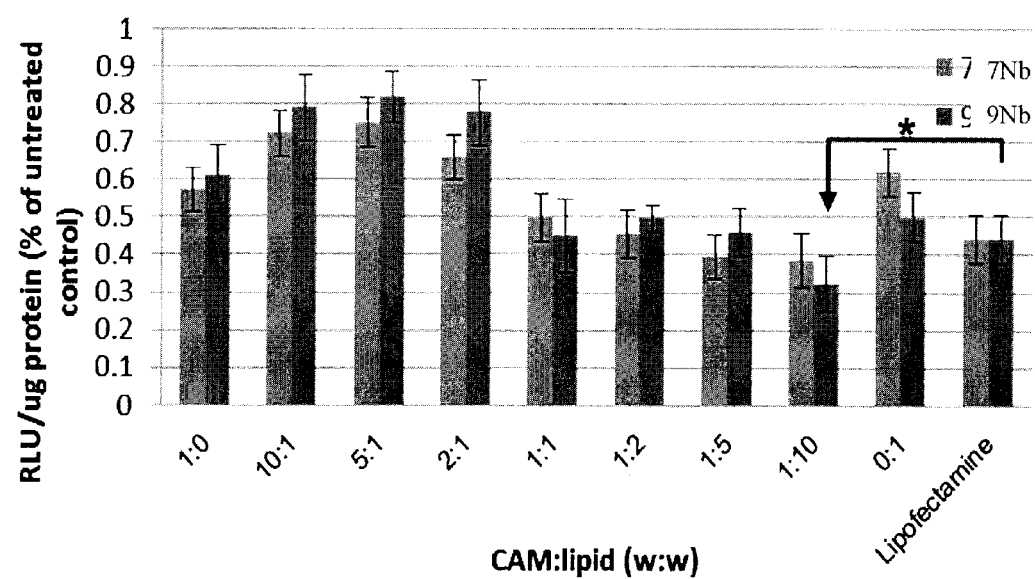
FIG. 8. Luciferase reporter gene down-regulation assay over 48 hrs performed in U87 luciferase cell line using complexes formulated from CAM-lipid complexes and anti-luciferase siRNA at N/P ratio of 50 (the 7Nb-lipid complex is represented by the light grey bar on the left and 9Nb-lipid complex is represented by the dark grey bar on the right for each ratio pairing). Lipofectamine is used as a control. Asterisks represent that 9Nb-lipid with weight ratio of 1:10 has significantly higher efficiency than Lipofectamine (p<0.05). Data represent mean±standard error (n=3).

To evaluate the gene silencing efficiency of CAM-lipid systems, the delivery of anti-luciferase siRNA to U87-Luc cells expressing luciferase was monitored. It was found that increasing CAM content in the complex compared to lipid alone resulted in a decreased transfection efficacy, as shown in FIG. 8. This finding is due to the fact that increasing CAM content will lead to a higher PEG coating percentage in the CAM-lipid complex which will eventually impede the cellular uptake of the complex. In contrast, increasing lipid content improved the gene silencing efficacy relative to CAMs alone. For those CAM-lipid complexes with weight ratios of 1:1, 1:2, and 1:5, gene silencing efficiencies were comparable with Lipofectamine. Among those conditions, the 9Nb-lipid with a weight ratio of 1:10 showed significantly higher gene silencing than Lipofectamine. It is speculated that this is due to the aforementioned synergistic effects between CAMs and lipids, which lead to enhanced transfection efficiency. Further mechanistic studies were conducted using the 9Nb-lipid with weight ratio of 1:10.

Figure 9:
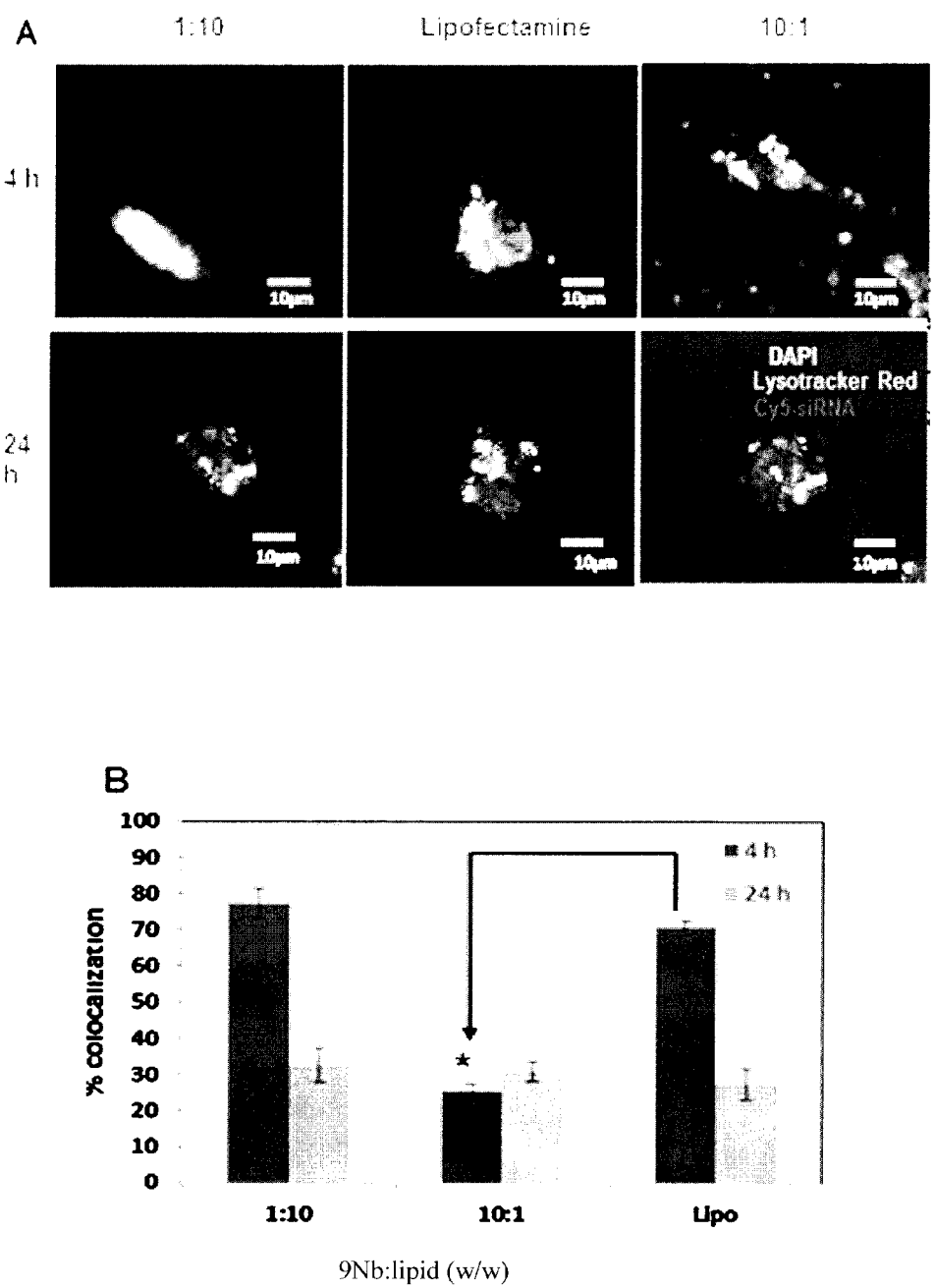
FIG. 9. (A) Confocal microscope images of Cy5-siRNA and endosomal distribution in U87 cells when delivered by the indicated 9Nb-lipid complexes or Lipofectamine 2000, at 4 h and 24 h post-transfection. (B) Colocalization of puncta was quantified using ImageJ. The % colocalization of Lysotracker Red and Cy5-siRNA puncta was calculated as mean gray value from colocalized points divided by mean gray value from sum of points using Image J. Data represent mean±standard error (n=3).

To further investigate the enhanced siRNA delivery observed for CAM-lipid mixtures, intracellular trafficking of several formulations was examined using confocal microscopy. As shown in FIG. 9, 9Nb-lipid/Cy5-siRNA at a weight ratio of 1:10 was co-localized with LysoTracker Red after 4 h of incubation. This observation suggests that the complexes were internalized but had not yet been released from endosomes or early lysosomes by 4 h. After 24 h, only minimal co-localization was observed and more extensive siRNA distribution was observed in the cytoplasm (data not shown), suggesting that Cy5-siRNA had undergone endosomal/lysosomal escape. When cells were stained with a plasma membrane marker, Cy5-siRNA puncta were only observed in the interior (data not shown). The same trends were observed when using Lipofectamine as the carrier. For the less effective carrier (CAM-lipid with weight ratio of 10:1), siRNA appeared to aggregate on the cell surface after 4 h. After 24 h, some CAM-lipid complexes were internalized, however, much more CAM-lipid complex remained on the cell surface as compared to the 1:10 formulation. These results suggest that siRNA efficiency is impaired at 10:1 weight ratio due to insufficient cell uptake and decreased intracellular release of siRNA. Therefore, to assure CAM-lipid complexes of optimized composition have great potential to be used as efficient non-viral carriers for siRNA delivery, cytotoxicity studies were conducted.

Figure 10:
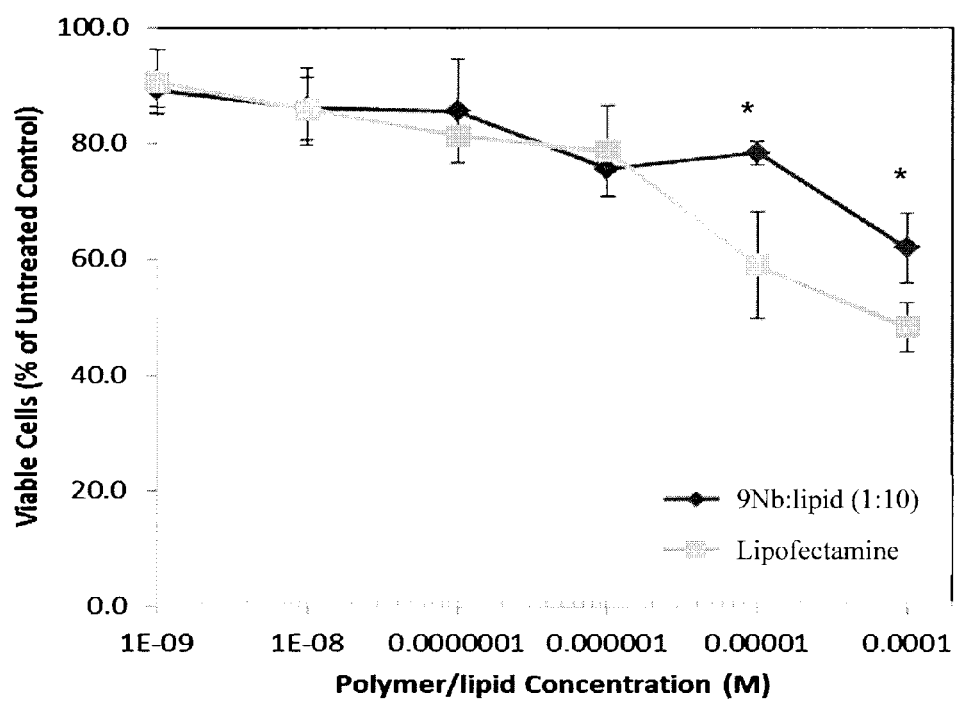
FIG. 10. Cytotoxicity of 9Nb-lipid (1:10 w/w) complexes was compared to Lipofectamine in U87 glioma cells after 72 h of exposure. Data represent mean±standard error (n=3). Asterisks represent concentrations at which CAM-lipid complexes elicited a significantly lower cytotoxicity than Lipofectamine (p<0.05).

Given the previous observation that CAM/siRNA complexes displayed low cytotoxicity (Sparks et al., Macromol Biosci, 11 (2011) 1192-1200), it is proposed herein that CAM-lipid/siRNA complexes would also be relatively benign to cells. To determine the effect of the concentration of 9Nb-lipid with weight ratio of 1:10 on cytotoxicity, an MTS assay was performed in U87 cells. FIG. 10 shows that no significant difference in cytotoxicity was observed between 9Nb-lipid/siRNA and Lipofectamine/siRNA at CAM-lipid concentrations less than $1\times10^{-5}$ M. At 9Nb-lipid complex concentrations of $1\times10^{-5}$ M and $1\times10^{-4}$ M, the viability was improved for 9Nb-lipid/siRNA compared to Lipofectamine, although in both cases a significant decrease in viability was observed compared to lower complex concentrations. As the concentration used for transfection was $2\times10^{-5}$ M 9Nb-lipid, it can be inferred that the enhanced endosomal escape and gene silencing ability of the 9Nb-lipid/siRNA (1:10 w/w) complexes compared to Lipofectamine is not due to a cytotoxic effect. Our new CAM-lipid system presented in this study demonstrates a high transfection efficacy and low cytotoxicity which can solve the dilemma between efficacy and cytotoxicity (Buyens et al., Journal of Controlled Release, 158 (2012) 362-370; Dang et al., Advanced Drug Delivery Reviews, 58 (2006) 487-499; and Aagaard et al., Advanced Drug Delivery Reviews, 59 (2007) 75-86) in non-viral delivery systems for in vivo applications. It is also notable that the hydrophobic portion of the CAM-lipid complexes can allow encapsulation of hydrophobic drugs or diagnostic tags. Herein, it is conceivable that CAM-lipid can be utilized as a multifunctional delivery system to achieve more therapeutic and diagnostic effects.

CONCLUSION

Novel CAM-lipid complexes were developed to deliver siRNA intracellularly. Langmuir monolayer and isothermal titration calorimetry were used to confirm the formation of stable CAM-lipid complexes. Size and zeta potential measurements further validate that CAM-lipid complexes are suitable for siRNA complexation and delivery. In vitro siRNA delivery experiments demonstrated that CAM-lipid complexes with specific CAM-lipid weight ratios have better or comparable gene silencing efficiencies as compared to a Lipofectamine control. Further intracellular trafficking and ITC studies revealed that siRNA can escape from endosomes and are released from CAM-lipid complexes to down-regulate genes. These studies strongly suggest that CAM-lipid complexes can serve as efficient siRNA delivery vehicles.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A compound of formula I:

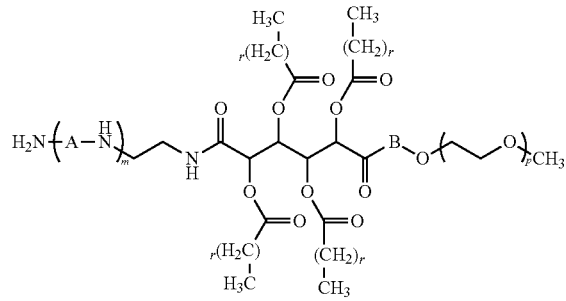

wherein:

B is the group —NH(-A-NH—)$_n$—(CH$_2$)$_2$—NH—C(=O)-D-;

each A is independently an ethylene group that is optionally substituted with one or more (C$_1$-C$_3$)alkyl groups;

D is (C$_1$-C$_6$)alkyl m is an integer from 0 to 100;

n is an integer from 0 to 100;

p is an integer from 1 to 200; and each r is independently an integer from 0 to 20;

or a salt thereof; and wherein the compound of formula I is not a compound of formula:

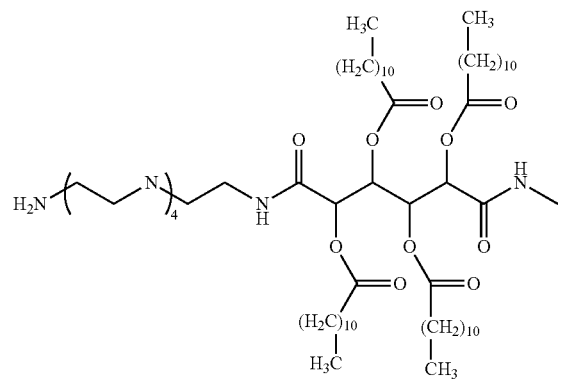

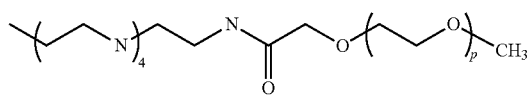

or a salt thereof.

2. The compound of claim 1 wherein B is —NH(-A-NH—)$_n$—(CH$_2$)$_2$—NH—C(=O)—CH$_2$CH$_2$—.

3. The compound of claim 1 wherein the compound of formula I is a compound formula I':

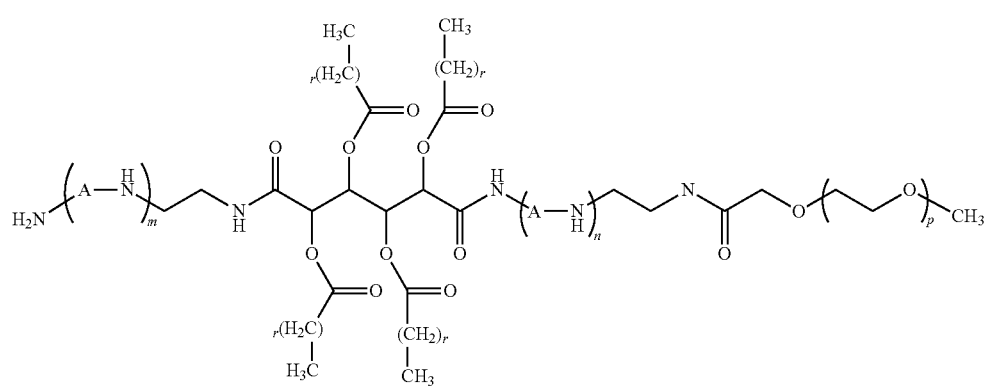

wherein:
  each A is independently an ethylene group that is optionally substituted with one or more $(C_1-C_3)$alkyl groups;
  m is an integer from 0 to 100;
  n is an integer from 0 to 100;
  p is an integer from 1 to 200; and
  each r is independently an integer from 0 to 20;
  or a salt thereof.

4. The compound of claim 1 wherein the compound of formula I is a compound formula I':

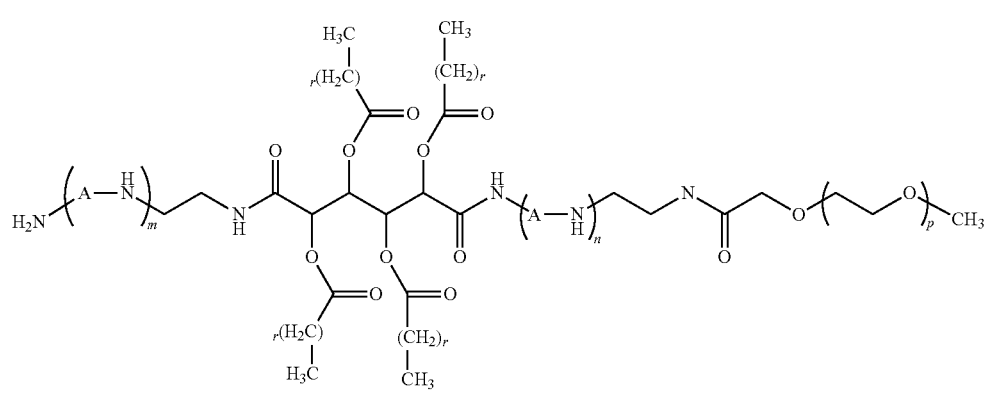

wherein:
  each A is independently an ethylene group that is optionally substituted with one or more $(C_1-C_3)$alkyl groups;
  m is an integer from 1 to 100;
  n is an integer from 1 to 100;
  p is an integer from 20 to 200; and
  each r is independently an integer from 0 to 20;
  or a salt thereof.

5. The compound of claim 1 wherein the compound of formula I is a compound of formula Ia:

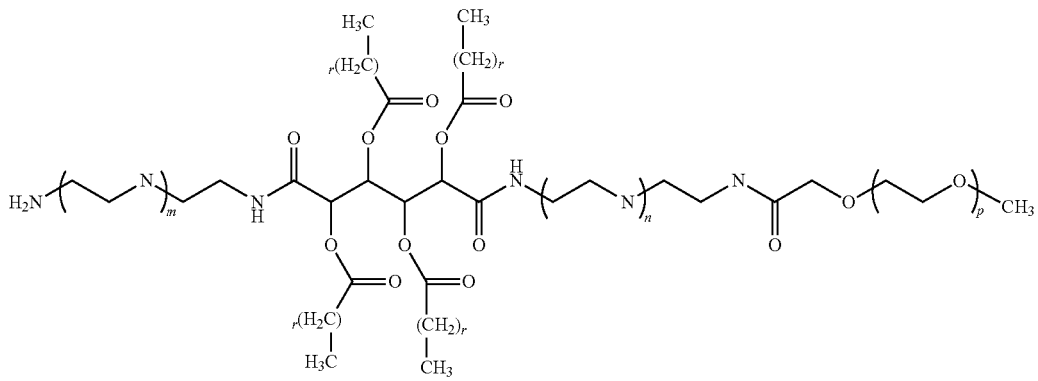

wherein:
  m is an integer from 0 to 100;
  n is an integer from 0 to 100;
  p is an integer from 1 to 200; and
  each r is independently an integer from 0 to 20;
  or a salt thereof.

6. The compound of claim 1 wherein the compound of formula I is a compound of formula Ia:

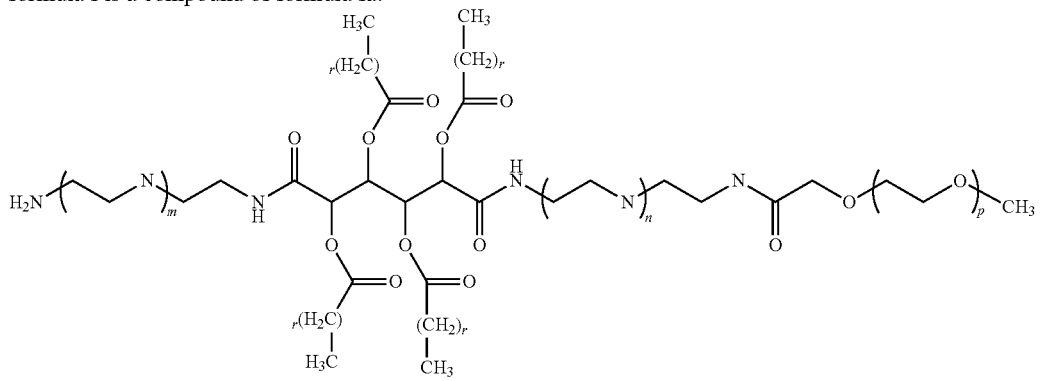

wherein:
  m is an integer from 1 to 100;
  n is an integer from 1 to 100;
  p is an integer from 20 to 200; and
  each r is independently an integer from 0 to 20;
or a salt thereof.

7. The compound of claim 1, wherein m is 0, 1, 2 or 3.

8. A compound of formula I:

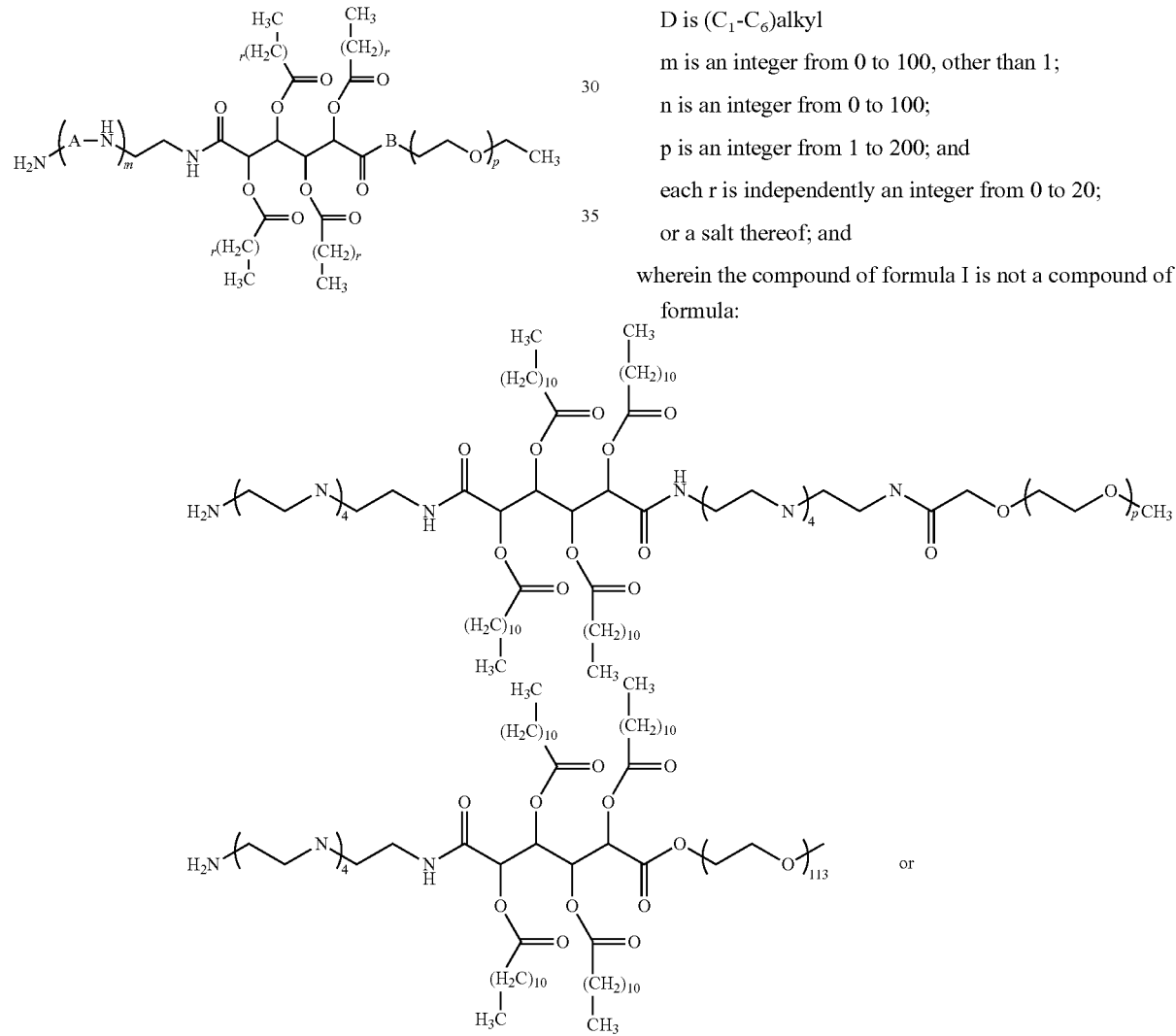

wherein:
  B is absent or the group —NH(-A-NH—)$_n$—(CH$_2$)$_2$—NH—C(=O)-D-;
  each A is independently an ethylene group that is optionally substituted with one or more (C$_1$-C$_3$)alkyl groups;
  D is (C$_1$-C$_6$)alkyl
  m is an integer from 0 to 100, other than 1;
  n is an integer from 0 to 100;
  p is an integer from 1 to 200; and
  each r is independently an integer from 0 to 20;
or a salt thereof; and wherein the compound of formula I is not a compound of formula:

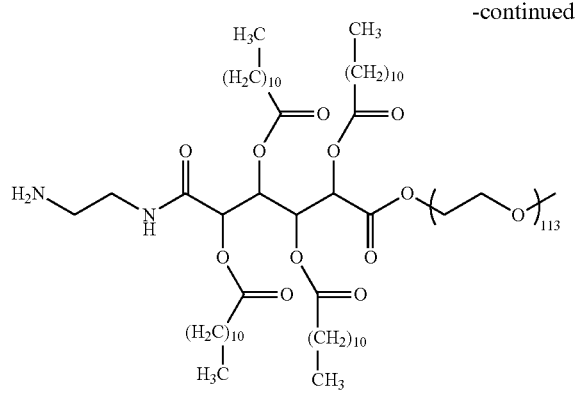

or a salt thereof.

9. The compound of claim 1 wherein m is an integer from 2 to 20 and n is an integer from 1 to 20.

10. The compound of claim 1 wherein m is 2, 3, or 4.

11. The compound of claim 1 wherein n is 1, 2, 3, or 4.

12. The compound of claim 1 wherein p is an integer from 20 to 200.

13. The compound of claim 1 wherein p is about 109.

14. The compound of claim 1 wherein each r is independently an integer from 0 to 20.

15. The compound of claim 1 wherein each r is independently 6, 7, 8, 9, 10, 11, 12, 13, 14, or 15.

16. The compound of claim 1 wherein: m is 2, 3, 4, or 5; n is 2, 3, 4, or 5; p is an integer from about 95 to about 125; and each r is independently 6, 7, 8, 9, 10, 11, 12, 13, 14, or 15.

17. The compound of claim 1 wherein the compound of formula I is a compound of formula Ib:

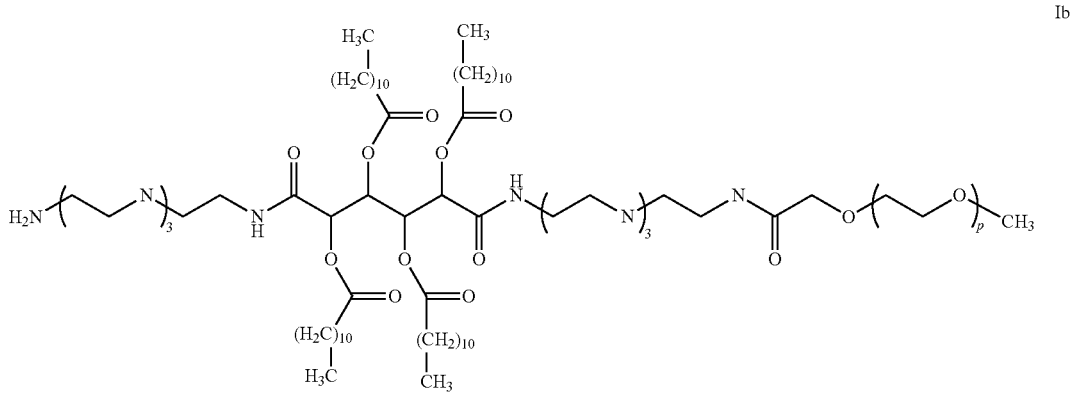

Ib or a salt thereof.

18. A compound of claim 1 which is:

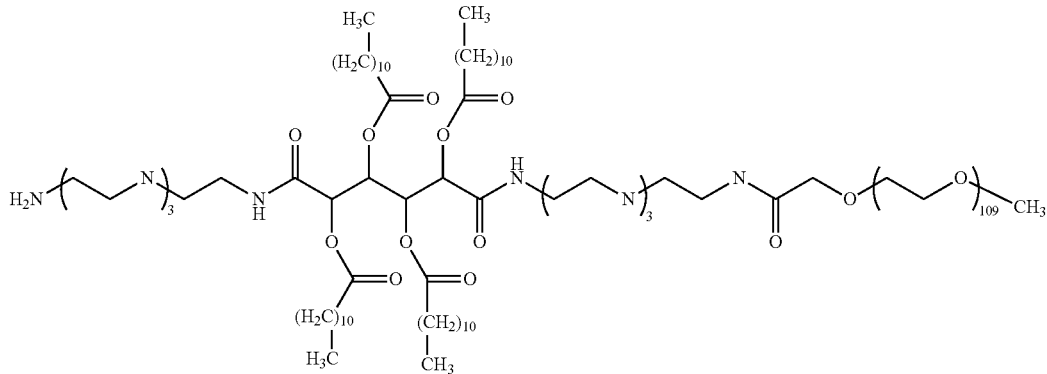

or a salt thereof.

19. A composition comprising a compound of formula I or a salt thereof as described in claim 1 and a nucleic acid.

20. The composition of claim 19 further comprising one or more lipids.

21. A method for delivering a nucleic acid into a cell comprising contacting the cell with a composition comprising a compound of formula I or a salt thereof as described in claim 1 and the nucleic acid under conditions such that the nucleic acid is delivered into the cell.

22. The method of claim 21 wherein the composition further comprises one or more lipids.

23. A compound of formula I:

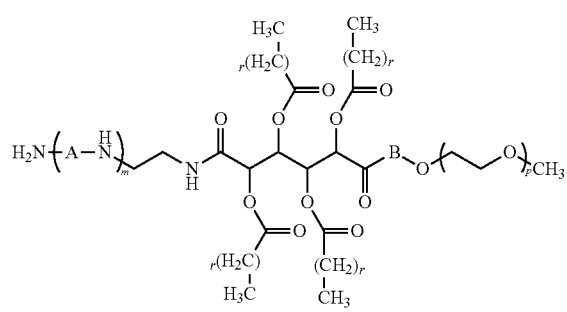

I wherein:
B is absent or the group —NH(-A-NH—)$_n$—(CH$_2$)$_2$—NH—C(=O)-D-;
each A is independently an ethylene group that is optionally substituted with one or more (C$_1$-C$_3$)alkyl groups;
D is (C$_1$-C$_6$)alkyl
m is an integer from 0 to 100;
n is an integer from 0 to 100;
p is an integer from 1 to 200; and
each r is independently an integer from 0 to 20, other than 10;
or a salt thereof.

24. A compound of formula I:

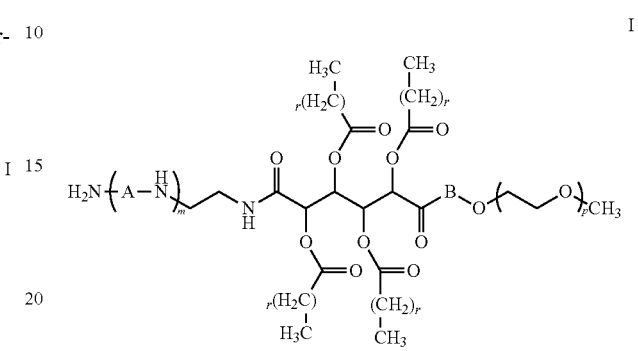

I wherein:
B is absent;
each A is independently an ethylene group that is optionally substituted with one or more (C$_1$-C$_3$)alkyl groups;
D is (C$_1$-C$_6$)alkyl
m is 2 or 3;
n is an integer from 0 to 100;
p is an integer from 1 to 200; and
each r is independently an integer from 0 to 20;
or a salt thereof.

* * * * *

UNITED STATES PATENT AND TRADEMARK OFFICE
CERTIFICATE OF CORRECTION

| | | |
|---|---|---|
| PATENT NO. | : 8,846,850 B2 | Page 1 of 1 |
| APPLICATION NO. | : 13/801562 | |
| DATED | : September 30, 2014 | |
| INVENTOR(S) | : Uhrich et al. | |

It is certified that error appears in the above-identified patent and that said Letters Patent is hereby corrected as shown below:

On the Title page, in Item (73) Assignee:

Replace:

Rutgers, the State University of New Jersey, New Brunswick, NJ (US)

With:

Rutgers, The State University of New Jersey, New Brunswick, NJ (US)

In the Specification

In Column 1, lines 14-17 under Government Funding:

Replace

The invention described herein was made with government support under Grant Number NIH R01 HL107913 awarded by the National Institutes of Health. The United States Government has certain rights in the invention.

With the following revised paragraph:

This invention was made with government support under NIH R01 HL107913 awarded by the National Institutes of Health. The government has certain rights in the invention.

Signed and Sealed this
Eighth Day of September, 2015

Michelle K. Lee
*Director of the United States Patent and Trademark Office*